US005861359A

United States Patent [19]

Theodoridis

[11] Patent Number: 5,861,359

[45] Date of Patent: Jan. 19, 1999

[54] HERBICIDAL PHENYLMETHOXPHENYL HETEROCYCLES

[75] Inventor: George Theodoridis, Princeton, N.J.

[73] Assignee: FMC Corporation, Phila., Pa.

[21] Appl. No.: 683,283

[22] Filed: Jul. 18, 1996

Related U.S. Application Data

[60] Provisional application No. 60/001,410, Jul. 25, 1995.

[51] Int. Cl.[6] .......................... A01N 43/56; C07D 231/20; C07D 231/16

[52] U.S. Cl. .......................... 504/282; 504/280; 548/366.1; 548/370.1; 548/370.4; 548/376.1

[58] Field of Search .......................... 548/366.1, 370.1, 548/370.4, 376.1; 504/280, 282

[56] References Cited

U.S. PATENT DOCUMENTS

| | | | |
|---|---|---|---|
| 5,032,165 | 7/1991 | Yuzo et al. | 71/92 |
| 5,262,390 | 11/1993 | Theodoridis | 71/92 |
| 5,344,812 | 9/1994 | Theodoridis | 504/243 |

OTHER PUBLICATIONS

Hampter, B. C., et al., J. Agric. Food Chem., 1995, 43, 219–228 "Synthesis and Herbicidal Activity of 3–Aryl–5–(haloalkyl)–4–isoxazolecarboxamides and Their Derivatives".

*Primary Examiner*—Patricia L. Morris
*Attorney, Agent, or Firm*—Donald J. Silvert; I. Robert Silverman; Rick Matos

[57] ABSTRACT

Novel herbicidal compounds, compositions containing them, and methods for their use in controling weeds are disclosed. The novel herbicidal compounds are optionally substituted phenylmethoxy or phenylmethylthio heterocycles of the formula:

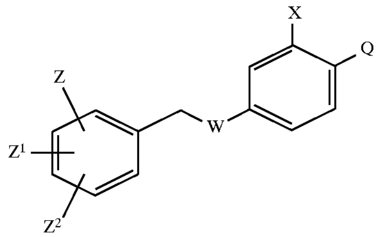

I in which Q is selected from:

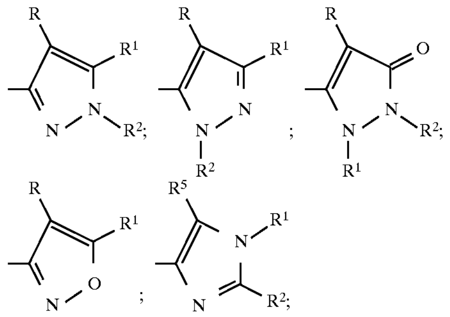

R=halogen; $R^1$=lower alkyl, lower alkoxy, lower haloalkyl, lower haloalkoxy, lower alkylthio, lower sulfonyl, or lower alkylsulfinyl; $R^2$=lower alkyl, or lower haloalkyl; X=H, halogen, or lower alkyl; W=O or S; Z, $Z^1$, $Z^2$ are independently selected from H, halogen, straight or branched chain lower alkyl, lower alkoxy, is lower haloalkoxy, cyano, lower cyanoalkyloxy, or aryl; or Z and $Z^1$ are adjacent to each other on the benzene ring, and taken together are $-(CH_2)_4-$; or $Z^2$ is OA in the 2-, 3-, or 4-position of the phenyl ring; A is a derivative of an alkanoate bonded to the phenoxy oxygen at the alpha carbon; $R^3$ is H or lower alkyl; $R^4$=OH or an agriculturally acceptable salt thereof, straight or branched chain lower alkoxy, lower haloalkoxy, alkoxyalkoxy, alkoxyalkoxyalkoxy, amino, lower alkylamino, lower alkylsulfonylamino, or lower (alkyl)(alkylsulfonyl)amino; and $R^5$=halogen or lower alkyl ester.

7 Claims, No Drawings

HERBICIDAL PHENYLMETHOXPHENYL HETEROCYCLES

BACKGROUND OF THE INVENTION

This application claims the benefit of the filing of U.S. Provisional Application Ser. No. 60/001410 filed Jul. 25, 1995.

The present invention relates generally to novel herbicidal compounds and methods for their use in controlling unwanted plant species in agriculture. In particular, the present invention relates to novel optionally substituted phenylmethoxyphenyl or phenylmethylthiophenyl heterocycles and their use as herbicides.

U.S. Pat. No. 5,032,165 (Miura et al.) discloses herbicidal (3-substituted phenyl)pyrazole derivatives of formula:

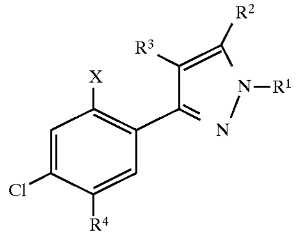

wherein:

X is halogen;

$R^1$ is lower alkyl or lower haloalkyl;

$R^2$ is —A—$R^5$ wherein $R^5$ is H, lower alkyl or lower haloalkyl, and A is O or S;

$R^3$ is H or halogen; and $R^4$ is formyl, nitro, —CO—B—$R^6$ [wherein B is O, S or —$NR^7$ and $R^6$ and $R^7$ are the same or different and each denote H, lower alkyl, lower alkenyl, lower alkynyl, lower alkoxycarbonylalkyl, cycloalkyl, lower alkylsulfonyl, lower alkoxyalkyl, or di(lower alkoxy) phosphinylalkyl, and when B is O, $R^6$ can be an alkali metal atom or a quaternary ammonium salt], —$DR^8$ [wherein D denotes O, —$S(O)_n$ (n being an integer of 0 to 2), or —$NR^9$—, and $R^8$ and $R^9$ are the same or different and each denote H, alkyl, haloalkyl, lower alkenyl, lower haloalkenyl, lower alkynyl, lower cyanoalkyl, lower cycloalkyl, lower alkoxyalkyl, lower alkylthioalkyl, lower alkoxyalkoxyalkyl, lower alkylsulfonyl, di(lower alkyl)aminosulfonyl, aminosulfonyl having one or more substituents which are the same or different and selected from H, lower alkynyl and lower alkyl, phenylalkyl or phenoxyalkyl optionally having on the phenyl ring, one or more substituents which are the same or different and selected from halogen, lower alkyl, lower haloalkyl and lower haloalkoxy, tri(lower alkyl)silylalkyl, or di(lower alkoxy)phosphinylalkyl]; or —$(CHR^{10})_m$—CO—E—$R^{12}$ [wherein E denotes O, S or —$NR^{11}$ wherein $R^{11}$ is as defined below; $R^{10}$ denotes H or lower alkyl; and $R^{11}$ and $R^{12}$ are the same or different and each denote H, alkyl, haloalkyl, lower alkenyl, lower haloalkenyl, lower alkynyl, lower haloalkynyl, lower alkoxyalkyl, cycloalkyl, lower cyanoalkyl, lower alkylthioalkyl, alkoxyalkoxyalkoxy, tri(lower alkyl)silylalkyl, di(lower alkoxy)phosphinylalkyl, phenyl optionally having on the phenyl ring, one or more substituents selected from halogen, lower alkyl, lower haloalkyl and lower alkoxy, or phenylalkyl optionally having on the phenyl ring, one or more substituents selected form halogen, lower alkyl, lower haloalkyl and lower alkoxy; or $R^{11}$ jointly with $R^{12}$ forms piperidino or morpholino, and when E is O, $R^{12}$ can be an alkali metal atom or a quaternary ammonium salt; and m is an integer of 0 to 3].

U.S. Pat. No. 5,262,390 (Theodoridis) discloses herbicidal 2-[(4-heterocyclic phenoxymethyl)phenoxy] alkanoates of formula:

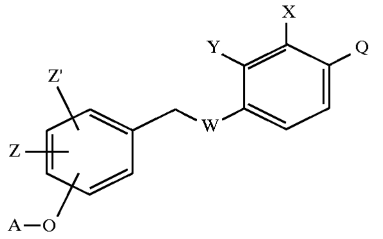

wherein:

A is a derivative of an alkanoate bonded to the phenoxy oxygen at the (α-carbon;

Q is a heterocycle selected from: 4-difluoromethyl-4,5-dihydro-3-methyl-1,2,4-triazol-5(1H)-on-1-yl, 3,4,5,6-tetrahydrophthalimid-1-yl, 1-(1-methylethyl) imidazolidin-2,4-dion-3-yl, 1,4-dihydro-4-(3-fluoropropyl)-5H-tetrazol-5-on-1-yl, 4-chloro-4,5,6,7-tetrahydroindazol-2-yl, 4-methyl-1,2,4-triazine-3,5-dion-2-yl, 8-thia-1,6-diazabicyclo[4. 3.0]nonane-7-on-9-ylimino, or 1-methyl-6-trifluoromethyl-2,4-pyrimidinedione-3-yl;

W is O or S;

X is H, F, or Cl; and Y is H, or X and Y taken together may be —$OC(CH_3)_2CH_2$— to form a 7-substituted-4-benzofuranyl moiety;

R' is H or methyl;

R" is —OR or amino, arylamino, alkylamino, alkenylamino, alkoxyamino, cyano or alkyl-, haloalkyl-, or arylsulfonylamino of the formula —N(lower alkyl)$SO_2R^9$, or —$NHSO_2R^9$;

R is H, M, alkyl, cycloalkyl, lower alkenyl, lower alkynyl, or —$[CHR^7(CH_2)_mO]_nR^8$;

Each of $R^1$ through $R^6$ are substituents on the heterocycle Q;

$R^7$ is H or lower alkyl;

$R^7$ is alkyl;

$R^9$ is alkyl, haloalkyl, or aryl;

m is 0 to 2;

M is a monovalent, salt-forming group;

Z is H, F, Cl, Br, lower alkyl, phenyl, or methoxy and Z' is H, F, or Cl; or Z and Z' taken together may be —$(CH_2)_4$— to form a tetrahydronaphthyl moiety; and the group —OA may be in the 2-, 3- or 4-position of the phenyl ring.

SUMMARY OF THE INVENTION

It has now been discovered that compounds of formula I of the present invention are unexpectedly active as pre- and post-emergence herbicides. In particular, the herbicides of the present invention exhibit tolerance of wheat, soybean and corn on both pre- and post-emergence applications. The compounds of the present invention are especially useful as pre-emergent herbicides.

DETAILED DESCRIPTION OF THE INVENTION

The novel optionally substituted phenylmethoxy or phenylmethylthio heterocycles of the present invention have the following generic structure:

I

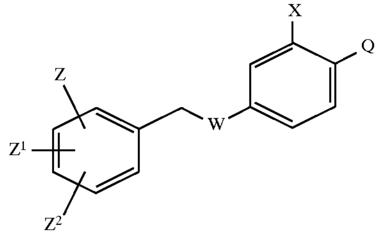

wherein:

Q is selected from the following heterocycles:

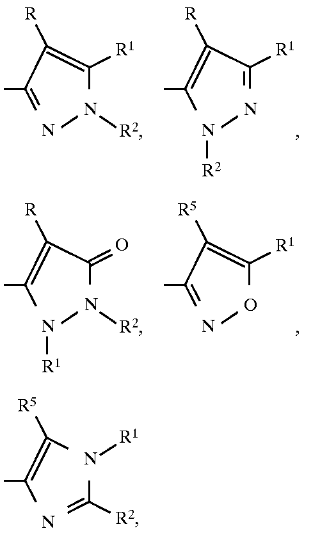

R=halogen or alkoxycarbonyl;

$R^1$=lower alkyl, lower alkoxy, lower haloalkyl, lower haloalkoxy, lower alkylthio, lower alkylsulfonyl, or lower alkylsulfinyl;

$R^2$=lower alkyl, or lower haloalkyl;

X=H, halogen, or lower alkyl;

W=O or S;

Z, $Z^1$, $Z^2$ are independently selected from H, halogen, straight or branched chain lower alkyl, lower haloalkyl, lower alkoxy, lower haloalkoxy, cyano, lower cyanoalkyloxy,nitro, aryl, or aryloxy; or Z and Z' are adjacent to each other on the benzene ring, and taken together are —$(CH_2)_4$—; or $Z^2$ is OA in the 2-, 3-, or 4- position of the phenyl ring;

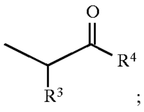

;

A is $R^3$ is H, lower alkyl, halo, or;

$R^4$=OH, straight or branched chain lower alkoxy, lower haloalkoxy, alkoxyalkoxy, alkoxyalkoxyalkoxy, alkoxycarbonylalkoxy, amino, lower alkylamino, lower alkoxyamino, lower alkylsulfonylamino, lower haloalkylsulfonylamino, lower (alkyl)(alkylsulfonyl) amino, or an agriculturally acceptable salt thereof; and $R^5$=halogen or lower alkyl ester.

As used herein, the following definitions shall apply. The term "alkyl" used alone or as part of a larger moiety shall include both straight and branched chains. The term "lower" used in connection with alkyl refers to $C_1$–$C_6$, preferably $C_1$–$C_4$ alkyl. The term "haloalkoxy" means alkoxy substituted with one or more halogen atoms. The term "halogen" preferably means F, Cl or Br.

Preferred compounds of the present invention include those of formula (I) wherein: Q=3-substituted pyrazole; W=O; Z=H, 4-alkyl or 4-halo; $Z^2$=—$OCH(CH_3)CO_2R^4$; and X=H or halogen. Particularly preferred compounds include those of formula (I) wherein: Q=3-substituted pyrazole; W=O; Z=4-ethyl, 4-methyl or 4-Cl; $Z^2$=2-$OCH(CH_3)CO_2$-alkyl; and X=H or F.

The compounds of the present invention may be prepared in general by methods known to those skilled in the art for analogous compounds, as illustrated in the schemes shown below.

SCHEME 1

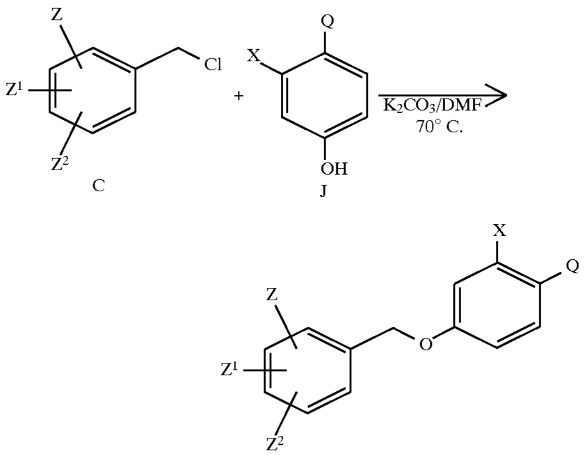

C J

I

Scheme 1 shows the coupling of J and C to provide I which contains the benzyloxy group and the heterocycle Q in a para orientation. In a similar manner to the coupling reaction shown in Scheme 1, J may be replaced by the corresponding thiophenol to obtain analogs of I wherein the $CH_2O$ bridge between the phenyl rings is replaced by $CH_2S$.

The substituted benzyl halide intermediates C may in turn be prepared as shown in Scheme 2 or in a similar manner depending on the substituent $Z^2$. If $Z^2$ is OA wherein A is an alkanoate ester, C may be obtained from a benzaldehyde such as B in two steps by reduction with sodium borohydride and chlorination with thionyl chloride. When $Z^2$ is OA, a convenient starting material is a substituted phenol which may be formylated to provide the 2-formylphenol A. Alkylation of A with an alkyl 2-haloalkanoate such as methyl 2-bromopropionate affords the alkyl (substituted-2-formylphenoxy)alkanoate ester B. Examples 1 and 2 provide detailed descriptions of the preparation of these intermediates.

SCHEME 2

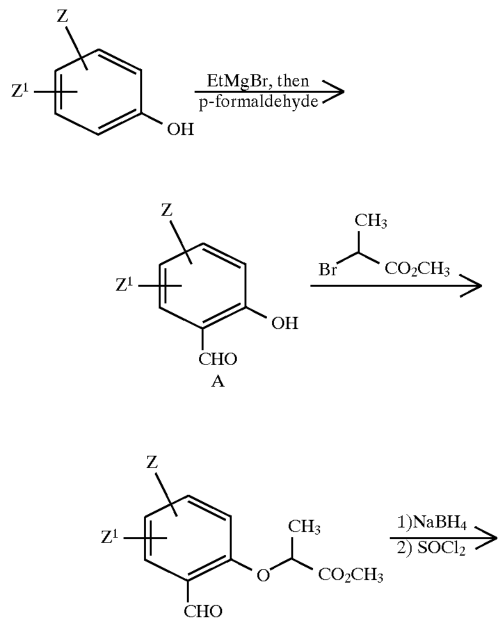

A

B

-continued

SCHEME 2

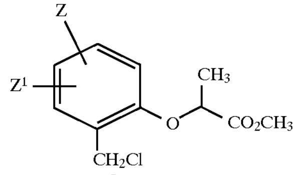

C

Among the useful intermediates for preparing many of the preferred compounds of the present invention are the following:

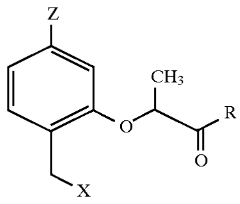 and 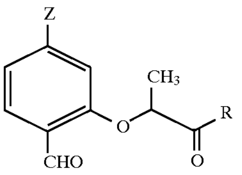

wherein X is Cl, Br, or OH;

Z is methyl, ethyl, chloro, bromo, or phenoxy; and

R is OH, straight or branched chain lower alkoxy, lower haloalkoxy, alkoxyalkoxy, alkoxyalkoxyalkoxy, alkoxycarbonylalkoxy, amino, lower alkylamino, lower dialkylamino, lower alkoxyamino, lower alkylsulfonylamino, lower haloalkylsulfonylamino, or lower (alkyl)(alkylsulfonyl)amino.

The various substituted phenol intermediates I may be prepared as depicted below in Scheme 3. Different methods were used depending upon the structure of substituent Q.

SCHEME 3A

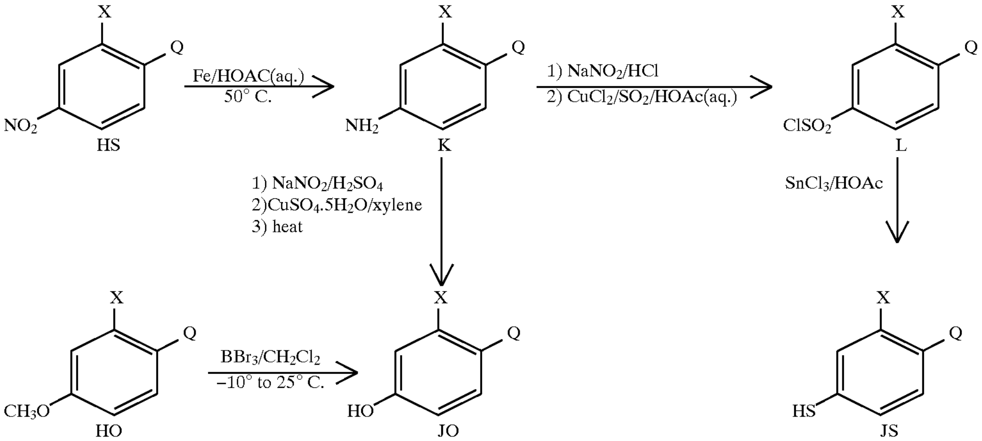

HS K L HO JO JS

Scheme 3A, above, illustrates how the phenol JO, for example, 4-(4-chloro-5-difluoromethoxy-1-methylpyrazol-3-yl)-3-fluorophenol, may be prepared. In one route, JO is obtained from HO by treatment with boron tribromide. Alternatively, HS can be reduced with iron powder and acetic acid in water, affording K. Compound K can then be diazotized with sodium nitrite under strong acidic conditions and treated with copper sulfate pentahydrate to yield the targeted intermediate JO. Examples 1 and 2 provide detailed descriptions of the preparation of these intermediates. To prepare the thiophenol JS, K can be diazotized with sodium nitrite and hydrochloric acid, then treated with copper(II) chloride and sulfur dioxide in acetic acid, to yield the corresponding 4-(pyrazol-3-yl)phenylsulfonyl chloride L. Compound L can then in turn be treated with tin(II) chloride in acetic acid, affording the targeted intermediate JS, for example, 4-(4-chloro-5-difluoromethoxyl-1-methylpyrazol-3-yl)thiophenol. Example 9 provides a detailed description of the preparation of this intermediate.

SCHEME 3B

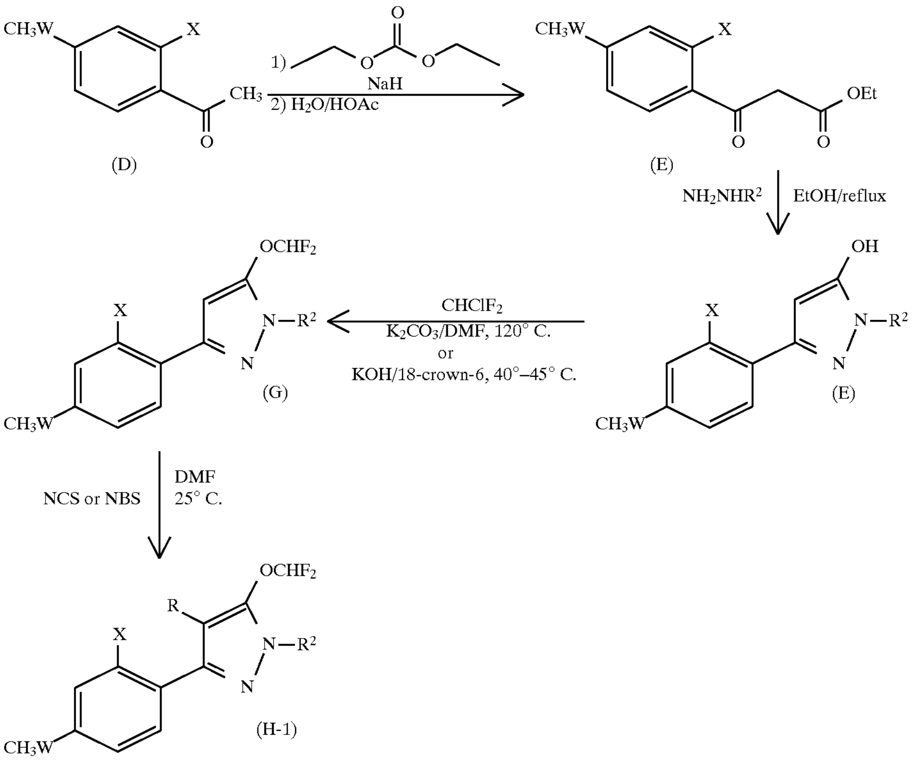

Scheme 3B above outlines a preparation of Compound H wherein Q is attached to the phenyl ring at position 3 of the pyrazole. A 2-substituted-4-methoxyacetophenone D may be treated with sodium hydride and diethyl carbonate, yielding the corresponding ethyl 3-(2-substituted-4-methoxyphenyl)-3-oxo-propionate E. Compound E is then cyclized with an alkyl hydrazine, for example, methylhydrazine, yielding a $^3$-(2-substituted-4-methoxyphenyl)-5-hydroxy-1-alkylpyrazole F. The intermediate F, is then reacted with a haloalkyl halide, for example, difluoromethyl chloride, affording the corresponding 3-(4-methoxyphenyl)-5-haloalkoxy-1-alkylpyrazole G. Compound G is in turn halogenated at the 4-position of the pyrazole ring with an N-halosuccinimide, affording Compound H, for example, 4-chloro-5-difluoromethoxy-3-(2-fluoro-4-methoxyphenyl)-1-methylpyrazole. The sequence outlined in Scheme 3B may also be carried out with intermediates wherein the $CH_3W$ group in compounds D through H in this sequence is replaced by a nitro group or other alkoxy groups, For example, the reactions outlined in Scheme 3B may be used to prepare 4-chloro-5-difluoromethoxy-1-methyl-3-(4-nitrophenyl)pyrazole. Example 1 provides a detailed description of the preparation of these intermediates.

In like fashion, Schemes 3C–3F, below, illustrate preparations of Compound H wherein Q is, respectively: 5-arylsubstituted pyrazole (Scheme 3C), substituted pyrazol-5-one (Scheme 3D), substituted isoxazole (Scheme 3E), and substituted imidazole (Scheme 3F).

SCHEME 3C

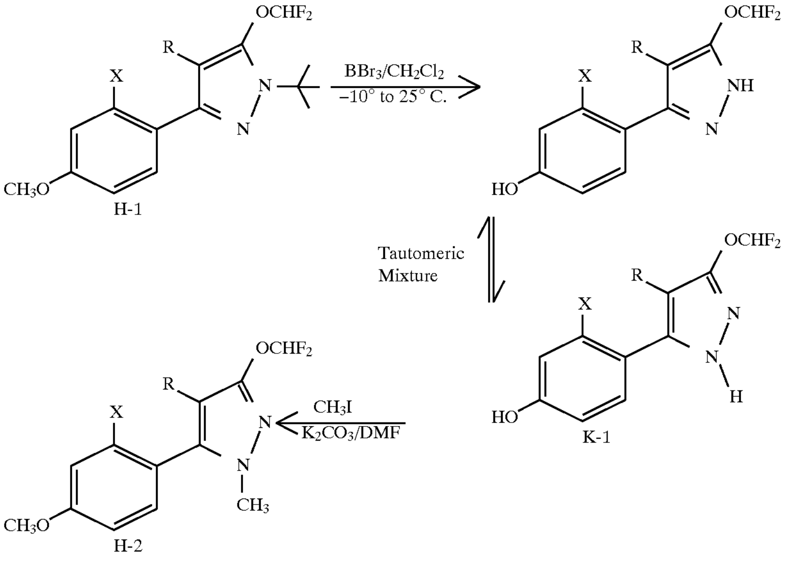

H-1, K-1, H-2

Scheme 3C illustrates a preparation of a tautomeric form of the pyrazoles wherein the aryl group is attached at the 5-position of the pyrazole ring rather than at the 3-position. Boron tribromide treatment of compound H-1 may be used to effect cleavage of alkyl groups attached to the phenolic oxygen and the N-1 position of the pyrazole ring resulting in a tautomeric mixture of pyrazoles. Alkylation of the tautomeric mixture with an alkyl halide such as iodomethane provides the dialkyated product H-2 as the major product. These reactions are described in detail in Example 11.

SCHEME 3D

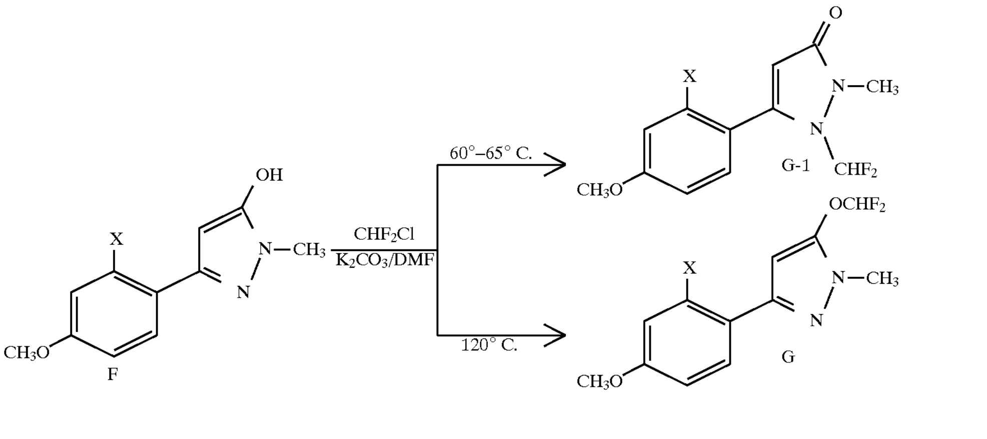

F, G-1, G

Scheme 3D illustrates how the dihydropyrazolone G-1 may be obtained. Heating the 5-hydroxypyrazole F in the presence of chlorodifluoromethane and potassium carbonate in DMF provides the N-alkylated product G-1 if the reaction is carried out at about 60–65° C. On the other hand, O-alkylation leading to G occurs when the reaction is carried out at about 120° C. Example 12 provides a detailed description for the preparation of G-1.

SCHEME 3E

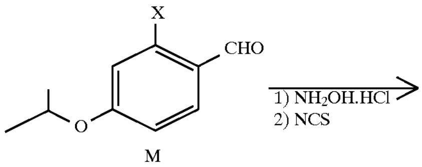

M

-continued

SCHEME 3E

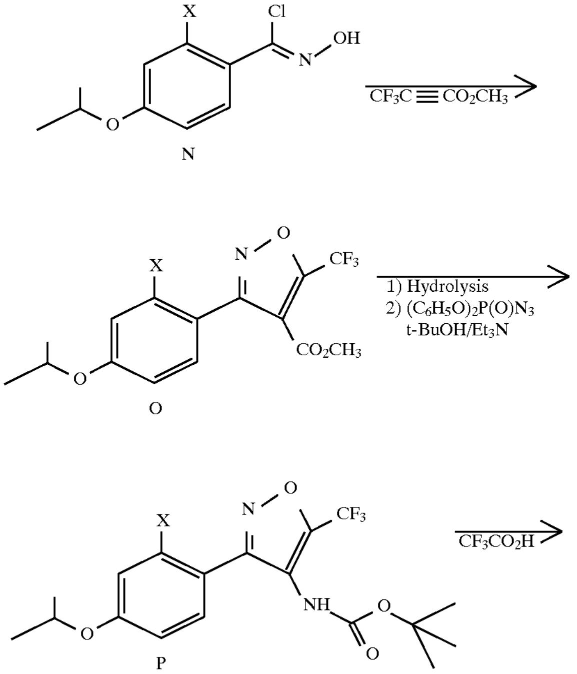

N

O

P

-continued

SCHEME 3E

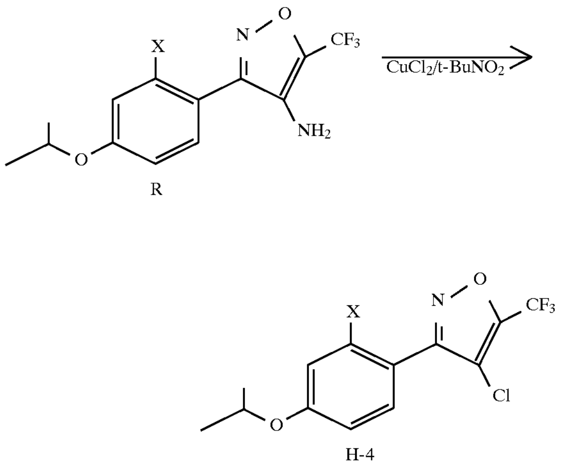

R

H-4

Scheme 3E illustrates how isoxazoles of the present invention may be prepared. The isoxazole ring may be constructed by the known procedures described in Example 13. The phenolic oxygen of intermediate H-4 may then be deprotected using boron tribromide as described above. Example 14 describes in detail the conversion of isozaxole intermediates to isoxazoles of the present invention.

SCHEME 3F

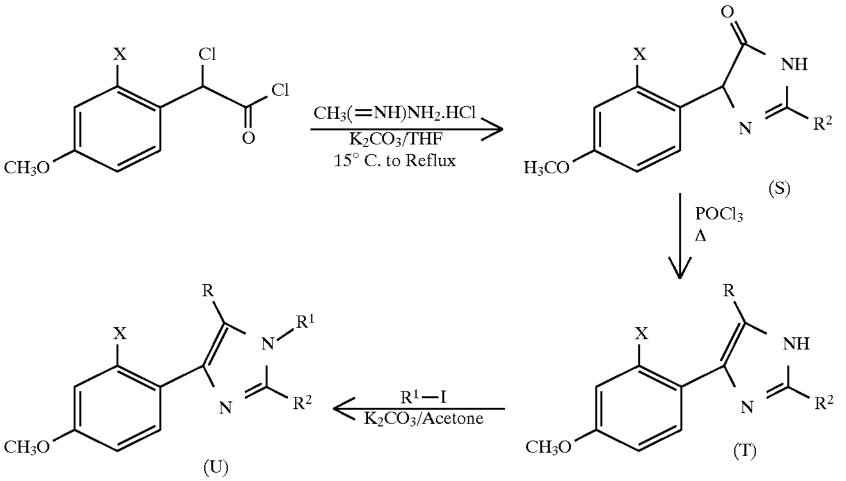

(S)

(T)

(U)

Scheme 3F illustrates a preparation of intermediates useful for making imidazoles of the present invention. A benzoylchloroacetylchloride may be condensed with the hydrazone of acetaldehyde to provide the dihydroimidazolone S. Intermediate U may be obtained by chlorination of S (to T) followed by N-alkylation of the imidazole ring of T. Example 15 provides a detailed description of these intermediates and their conversion to imidazoles of the present invention.

As depicted below in Scheme 4, certain of the compounds of the present invention are also useful as intermediates for other compounds within the scope of the present invention. For example, where $Z^2$ is the moiety —OA in the 2- 3-, or 4-position of the phenyl ring, the alkyl ester I-A may be hydrolyzed with aqueous sodium hydroxide which, upon neutralization, provides the corresponding alkanoic acid I-B (for example, 2-[2-[4-(4-chloro-5-difluoromethoxyl-1-methylpyrazol-3-yl)phenoxymethyl]-5-methylphenoxy] propanoic acid or 2-[5-ethyl-2-[4-(4-chloro-5-difluoromethoxyl-1-methylpyrazol-3-yl)phenoxymethyl]-phenoxy]propanoic acid. The acid I-B may then be esterified with an alkyl iodide in the presence of 1,8-diazobicyclo [5.4.0]undec-7-ene ("DBU") affording, for example, ethyl 2-[2-[4-(4 -chloro-5-difluoromethoxyl-1-methylpyrazol-3-yl)phenoxymethyl]-5-methylphenoxy]propanoate. Alternatively I-B may be converted to the acid chloride I-C and treated with various alcohols or amines as may be required for preparing compounds of the present invention. Examples 4–8 provide detailed descriptions of the preparation of these compounds.

SCHEME 4

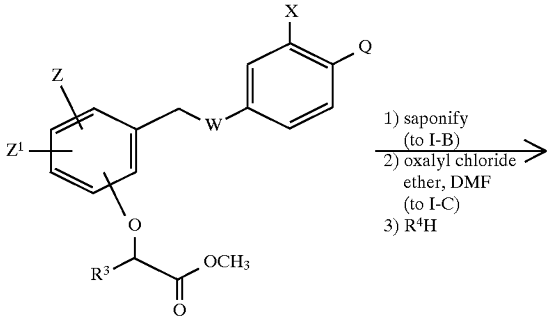

I-A

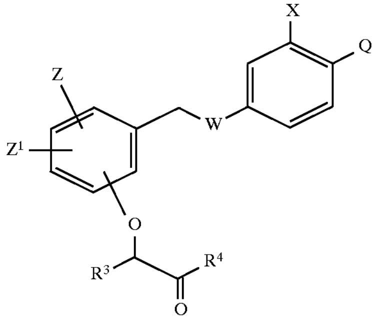

I

The ester moiety —OA in the 2-, 3-, or 4-position of the phenyl ring of I-A may also be subjected to transesterification conditions to prepare other, more complex esters. For example, methyl 2-[5-ethyl-2-[3-fluoro-4-(4-chloro-5-difluoromethoxyl-1-methylpyrazol-3-yl]phenoxymethyl] phenoxy]propanoate is reacted with 2-(2-methoxyethoxy) ethanol in the presence of titanium (IV) isopropoxide, yielding the corresponding 2-(2-methoxyethoxy)ethyl 2-[5-ethyl-2-[3-fluoro-4-(4-chloro-5-difluoromethoxyl-1-methylpyrazol-3-yl]phenoxymethyl]phenoxy]propanoate. Example 10 provides a detailed description of the preparation of this compound.

EXAMPLE 1

Synthesis of Methyl 2-[5-ethyl-2-[3-fluoro-4-(4-chloro-5-difluoromethoxy-1-methylpyrazol-3-yl) phenoxymethyl]-phenoxy]propanoate (Compound 103)

Step A Synthesis of 5-ethyl-2-formylphenol as an intermediate

A stirred solution of 200 mL (0.20 mole) of 1.0M of ethylmagnesium bromide (in tetrahydrofuran) in 100 mL of tetrahydrofuran was cooled in an ice-bath and 25.0 grams (0.21 mole) of 3-ethylphenol was added dropwise. Upon completion of addition, the reaction mixture was allowed to warm to ambient temperature where it stirred for 30 minutes. After this time, 15.4 grams (0.51 mole) of paraformaldehyde, 36.7 grams (0.21 mole) of hexamethylphosphoramide, and 350 mL of toluene were added. Upon completion of addition, the reaction mixture was heated to 80° C. where it stirred for about 18 hours. The reaction mixture was then cooled and concentrated under reduced pressure to a residue. The residue was taken up in diethyl ether and 200 mL of an aqueous 10% hydrochloric acid solution was added. The aqueous layer was separated and extracted with diethyl ether. The extract was combined with the organic layer, and the combination was washed with water. The organic layer was dried with magnesium sulfate and filtered. The filtrate was concentrated under reduce pressure to a residue. The residue was subjected to column chromatography on silica gel, using 1:1 hexane and methylene chloride as the eluant. The product-containing fractions were combined and concentrated under reduced pressure, yielding 21.8 grams of 5-ethyl-2-formylphenol. The NMR spectrum was consistent with the proposed structure.

Step B Synthesis of methyl 2-(5-ethyl-2-formylphenoxy) propanoate as an intermediate A stirred solution of 21.8 grams (0.15 mole) of 5-ethyl-2-formylphenol, 24.2 grams (0.15 mole) of methyl DL-2-bromopropanoate, and 30 grams (0.22 mole) of potassium carbonate in 300 mL of acetone was heated at reflux for about 18 hours. After this time, the reaction mixture was cooled and concentrated under reduced pressure to a residue. The residue was taken up in methylene chloride, washed first with water, and then with an aqueous 10% sodium hydroxide solution. The organic layer was dried with magnesium sulfate and filtered. The filtrate was concentrated under reduced pressure to a residue. The residue was subjected to column chromatography on silica gel, using a gradient elution starting with 50% methylene chloride in hexane and progressing to 100% methylene chloride. The product-containing fractions were combined and concentrated under reduced pressure, yielding 9.8 grams of methyl 2-(5-ethyl-2-formylphenoxy)propanoate. The NMR spectrum was consistent with the proposed structure.

Step C Synthesis of methyl 2-(2-chloromethyl-5-ethylphenoxy)propanoate as an intermediate A stirred solution of 0.2 gram (0.004 mole) of sodium methoxide in 20 mL of methanol was cooled to about 5° C., and a solution of 4.7 grams (0.020 mole) of methyl 2-(5-ethyl-2-formylphenoxy)propanoate in 30 mL of methanol was added. Upon completion of addition, 0.2 gram (0.006 mole) of sodium borohydride was added. The reaction mixture was then allowed to warm to ambient temperature where it stirred for one hour. After this time the reaction mixture was poured into 40 mL of aqueous 0.25N hydrochloric acid solution. The mixture was extracted with methylene chloride, and the combined extracts were concentrated under reduced pressure to a residue. The residue was purified using column chromatography, yielding methyl 2-(5-ethyl-2-hydroxymethylphenoxy)propanoate. The methyl 2-(5-ethyl-2-hydroxymethylphenoxy)propanoate, 1.1 grams (0.005 mole), was dissolved in 60 mL of methylene chloride, and one drop of pyridine and 0.4 mL of thionyl chloride were added. Upon completion of addition, the reaction mixture was warmed to 50° C. where it stirred for about two hours. After this time the reaction mixture was allowed to cool to ambient temperature. The reaction mixture was then washed with water and dried with magnesium sulfate. The mixture was filtered, and the filtrate was passed through a pad of silica gel. The eluate was concentrated under reduced pressure, yielding 0.9 gram of title compound.

Step D Synthesis of ethyl 3-(2-fluoro-4-methoxyphenyl)-3-oxopropanoate as an intermediate.

A stirred solution of 9.5 grams (0.05 mole) of 2'-fluoro-4'-methoxyaceto-phenone in 100 mL of diethyl carbonate was cooled to 10° C., and 4.1 grams (0.10 mole) of 60% sodium hydride (in mineral oil) was added in one portion. The reaction mixture was allowed to slowly warm to ambient temperature, then it was warmed to 60° C. where it stirred for about 1.5 hours. After this time, the reaction mixture was poured into 500 mL of ice-cold water which contained 20 mL of acetic acid. The mixture was extracted with diethyl ether, and the combined extracts were dried with magnesium sulfate. The mixture was filtered, and the filtrate was concentrated under reduced pressure to a residue. The residue was subjected to column chromatography on silica gel, using methylene chloride as the eluant, The product-containing fractions were combined and concentrated under reduced pressure, yielding 9.5 grams of title compound. The NMR spectrum was consistent with the proposed structure. This reaction was repeated several times.

Step E Synthesis of 3-(2-fluoro-4-methoxyphenyl)-5-hydroxy-1-methyl-pyrazole as an intermediate.

A stirred solution of 22.0 grams (0.09 mole) of ethyl 3-(2-fluoro-4-methoxyphenyl)-3-oxopropanoate and 4.6 grams (0.10 mole) of methylhydrazine in 100 mL of ethanol was heated at reflux for about 18 hours. After this time, the reaction mixture was concentrated under reduced pressure to a residual solid. The solid was washed with water and dried, yielding 18.5 grams of title compound, mp 133–135° C. The NMR spectrum was consistent with the proposed structure.

Step F Synthesis of 5-difluoromethoxy-3-(2-fluoro-4-methoxyphenyl)-1-methylpyrazole as an intermediate.

A stirred solution of 17.0 grams (0.08 mole) of 3-(2-fluoro-4-methoxyphenyl)-5-hydroxy-1-methylpyrazole and 32.0 grams (0.23 mole) of potassium carbonate in 120 mL of N,N-dimethylformamide was warmed to 120° C., and chlorodifluoromethane was bubbled through the reaction mixture during a 30 minute period. After this time the reaction mixture was poured into water. The mixture was extracted with diethyl ether, and the combined extracts were dried with magnesium sulfate. The mixture was filtered and the filtrate was concentrated under reduced pressure to a residue. The residue was purified by column chromatography. The product-containing fractions were combined and concentrated under reduced pressure, yielding 7.4 grams of title compound, mp 51–53° C. The NMR spectrum was consistent with the proposed structure.

Step G Synthesis of 4-chloro-5-difluoromethoxy-3-(2-fluoro-4-methoxy-phenyl)-1-methylpyrazole as an intermediate.

A solution of 6.2 grams (0.023 mole) of 5-difluoromethoxy-3-(2-fluoro-4-methoxyphenyl)-1-methylpyrazole and 3.0 grams (0.023 mole) of N-chlorosuccinimide in 100 mL of N,N-dimethylformamide was stirred at ambient temperature for about 18 hours. The reaction mixture was then poured into water, and the mixture was extracted with ethyl acetate. The combined extracts were dried with magnesium sulfate and filtered. The filtrate was concentrated under reduced pressure to a residue. The NMR spectrum of the residue indicated that 20–30% of the starting material was unreacted. The residue was dissolved in fresh N,N-dimethylformamide and 1.1 grams (0.006 mole) of N-chlorosuccinimide was added. The reaction mixture was stirred at ambient temperature for an additional 18 hours. The reaction mixture was worked up as described above, yielding a residue. The residue was subjected to column chromatography on silica gel, using 1:9 heptane:methylene chloride as the eluant. The product-containing fractions were combined and concentrated under reduced pressure, yielding 4.0 grams of title compound.

Step H Synthesis of 4-(4-chloro-5-difluoromethoxy-1-methylpyrazol-3-yl)-3-fluorophenol as an intermediate A stirred solution of 26 mL (0.026 mole) of 1M boron tribromide (in methylene chloride) in 50 mL of methylene chloride was cooled to −10° C., and 4.0 grams (0.013 mole) of 4-chloro-5-difluoromethoxy-3-(2-fluoro-4-methoxyphenyl)-1-methylpyrazole was slowly added. Upon completion of addition, the reaction mixture was allowed to warm to ambient temperature where it stirred for about 18 hours. The reaction mixture was then poured into ice and extracted with methylene chloride. The combined extracts were dried with magnesium sulfate and filtered. The filtrate was concentrated under reduced pressure, yielding 3.2 grams of title compound, mp 111–112° C. The NMR spectrum was consistent with the proposed structure.

Step I Synthesis of methyl 2-[5-ethyl-2-[3-fluoro-4-(4-chloro-5-difluoro-methoxy-1-methylpyrazol-3-yl)phenoxymethyl]phenoxy]propanoate (Compound 103)

A stirred solution of 0.8 gram (0.003 mole) of 4-(4-chloro-5-difluoromethoxy-1-methylpyrazol-3-yl)-3-fluorophenol, 0.7 gram (0.003 mole) of methyl 2-(2-chloromethyl-5-ethylphenoxy)propanoate (prepared in Steps A through C of this Example), and 0.4 gram (0.003 mole) of potassium carbonate in 40 mL of N,N-dimethylformamide was heated at 70° C. for about 18 hours. After this time the reaction mixture was allowed to cool to ambient temperature, then it was poured into ice. The mixture was extracted with two 100 mL portions of diethyl ether. The combined extracts were dried with magnesium sulfate, filtered, and concentrated under reduced pressure to a residue. The residue was purified using column chromatography to provide the title compound (yield 1.4 grams). The NMR spectrum was consistent with the proposed structure.

EXAMPLE 2

Synthesis of Methyl 2-[5-chloro-2-[4-(4-chloro-5-difluoromethoxy-1-methylpyrazol-3-yl)phenoxymethyl]phenoxy]propanoate (Compound 32)

Step A Synthesis of 5-chloro-2-formylphenol as an intermediate.

This compound was prepared in a manner analogous to that of Step A of Example 1, using 20.0 grams (0.156 mole)

of 3-chlorophenol, 156 mL (0.156 mole) of 1.0M ethylmagnesium bromide (in tetrahydrofuran), 11.7 grams (0.39 mole) of paraformaldehyde, 27.9 grams (0.156 mole) of hexamethylphosphoramide, 100 mL of tetrahydrofuran, and 350 mL of toluene. The yield of 5-chloro-2-formylphenol was 9.3 grams. The NMR spectrum was consistent with the proposed structure.

Step B Synthesis of methyl 2-(5-chloro-2-formylphenoxy)propanoate as an intermediate.

This compound was prepared in a manner analogous to that of Step B of Example 1, using 9.3 grams (0.059 mole) of 5-chloro-2-formylphenol, 11.8 grams (0.071 mole) of methyl DL-2-bromopropanoate, 9.8 grams (0.071 mole) of potassium carbonate, and 100 mL of 2-butanone. The yield of title compound was 11.6 grams. The NMR spectrum was consistent with the proposed structure.

Step C Synthesis of methyl 2-(5-chloro-2-hydroxymethylphenoxy)propanoate as an intermediate.

This compound was prepared in a manner analogous to that of the first part of Step C of Example 1, using 11.60 grams (0.049 mole) of methyl 2-(5-chloro-2-formylphenoxy-propanoate, 0.16 gram (0.003 mole) of sodium methoxide, and 0.40 gram (0.012 mole) of sodium borohydride in 100 mL of methanol. The yield of title compound was 11.50 grams. The NMR spectrum was consistent with the proposed structure.

Step D Synthesis of methyl 2-(5-chloro-2-chloromethylphenoxy)propanoate as an intermediate.

This compound was prepared in a manner analogous to that of the second part of Step C of Example 1, using 7.6 grams (0.031 mole) of methyl 2-(5-chloro-2-hydroxymethylphenoxy)propanoate, 5.5 grams (0.047 mole) of thionyl chloride, and 1.0 mL of pyridine in 100 mL of diethyl ether. The yield of title compound was 8.0 grams. The NMR spectrum was consistent with the proposed structure.

Step E Synthesis of 5-hydroxy-1-methyl-3-(4-nitrophenyl)pyrazole as an intermediate.

This compound was prepared in a manner analogous to that of Step E of Example 1, using 25.0 grams (0.105 mole) of ethyl 3-(4-nitrophenyl)-3-oxopropanoate (commercially available) and 5.5 grams (0.120 mole) of methylhydrazine in 150 mL of ethanol. The yield of title compound was about 21.6 grams, mp 249–251° C. This reaction was repeated a second time, yielding an additional 22.8 grams of material.

Step F Synthesis of 5-difluoromethoxy-1-methyl-3-(4-nitrophenyl)pyrazole as an intermediate.

This compound was prepared in a manner analogous to that of Step F of Example 1, using 43.0 grams (0.20 mole) of 5-hydroxy-1-methyl-3-(4-nitrophen-yl)pyrazole, gaseous chlorodifluoromethane (excess), and 138.0 grams (1.0 mole) of potassium carbonate in N,N-dimethylformamide. The yield of title compound was 30.0 grams, mp 105–107° C. The NMR spectrum was consistent with the proposed structure.

Step G Synthesis of 4-chloro-5-difluoromethoxy-1-methyl-3-(4-nitro-phenyl)pyrazole as an intermediate.

This compound was prepared in a manner analogous to that of Step G of Example 1, using 2.7 grams (0.01 mole) of 5-difluoromethoxy-1-methyl-3-(4-nitrophenyl)pyrazole and 1.3 grams (0.01 mole) of N-chlorosuccinimide in N,N-dimethylformamide. The yield of title compound was 2.8 grams, mp 117–119° C. This reaction was repeated two times, yielding an additional 2.9 grams and 29.4 grams of material.

Step H Synthesis of 3-(4-aminophenyl)-4-chloro-5-difluoromethoxy-1-methylpyrazole as an intermediate.

A stirred solution of 28.0 grams (0.93 mole) of 4-chloro-5-difluoromethoxy-1-methyl-3-(4-nitrophenyl)pyrazole and 20 mL of water in 150 mL of acetic acid was warmed to 50° C., and 28.0 grams (excess) of iron powder was added slowly during a 30 minute period. Upon completion of addition, the reaction mixture was allowed to cool to ambient temperature where it stirred for one hour. The reaction mixture was stirred with about 300 mL of water and 300 mL of ethyl acetate, then filtered through a pad of diatomaceous earth. The aqueous layer was extracted with ethyl acetate, and the combined extracts were dried with magnesium sulfate. The mixture was filtered, and the filtrate was concentrated under reduced pressure to a residue. The residue was subjected to column chromatography on silica gel, using 9.5/0.5 methylene chloride and ethyl acetate as the eluant. The product-containing fractions were combined and concentrated under reduced pressure, yielding 18.0 grams of title compound.

Step I Synthesis of 4-(4-chloro-5-difluoromethoxy-1-methylpyrazol-3-yl)phenol as an intermediate.

A stirred solution of 6.0 grams (0.022 mole) of 3-(4-aminophenyl)-4-chloro-5-difluoromethoxy-1-methylpyrazole in 125 mL of concentrated sulfuric acid was cooled to 10° C., and a solution of 1.7 grams (0.024 mole) of sodium nitrite in 10 mL of water was added dropwise at a rate to maintain the reaction mixture temperature at 10–13° C. Upon completion of addition, the reaction mixture was allowed to warm to ambient temperature where it stirred for one hour. In a second reaction vessel, a stirred mixture of 125.8 grams (0.50 mole) of copper sulfate pentahydrate and 125 mL of water in 125 mL of p-xylene was heated to reflux, and the diazotization product in the first reaction vessel was added to the second vessel. Upon completion of addition, the reaction mixture was stirred at reflux for an additional 20 minutes. The reaction mixture was then cooled and the xylene layer was separated. The xylene layer was extracted with a solution of 10.0 grams of sodium hydroxide dissolved in 125 mL of water. The aqueous extract was then neutralized and extracted with diethyl ether. The combined diethyl ether extracts were concentrated under reduced pressure to a small amount of residue. The original aqueous layer from the reaction mixture was extracted with two portions of ethyl acetate. The extracts were combined with the residue from the xylene layer, and the combination was dried with magnesium sulfate. The mixture was filtered, and the filtrate was concentrated under reduced pressure to a residue. The residue was subjected to column chromatography on silica gel, using a gradient elution of 50% ethyl acetate in heptane to 100% ethyl acetate. The product-containing fractions were combined and concentrated under reduced pressure, yielding a viscous oil residue. The residue was triturated with ethyl acetate and heptane to form a solid. The solid was collected by filtration and dried, yielding 3.7 grams of title compound, mp 159–161° C. The NMR spectrum was consistent with the proposed structure.

Step J Synthesis of methyl 2-[5-chloro-2-[4-(4-chloro-5-difluoromethoxy-1-methylpyrazol-3-yl)phenoxymethyl]phenoxy]propanoate (Compound 32)

This compound was prepared in a manner analogous to that of Step I of Example 1, using 0.82 gram (0.0030 mole) of 4-(4-chloro-5-difluoromethoxy-1-methylpyrazol-3-yl)phenol, 0.95 gram (0.0036 mole) of methyl 2-(5-chloro-2-chloromethylphenoxy)propanoate (prepared in Steps A through D of this Example), and 0.62 gram (0.0045 mole) of potassium carbonate in N,N-dimethylformamide. The crude reaction product was subjected to column chromatography on silica gel, using 1:4 ethyl acetate and heptane as the eluant. The product-containing fractions were combined and concentrated under reduced pressure to an oil. The oil was triturated with heptane, yielding 0.68 gram of title compound, mp 61–64° C. The NMR spectrum was consistent with the proposed structure.

EXAMPLE 3

Synthesis of 4-chloro-3-[2-fluoro-4-(4-chlorophenyl-methoxy)phenyl]-5-difluoromethoxy-1-methylpyrazole (Compound 20)

This compound was prepared in a manner analogous to that of Step I of Example 1, using 0.59 gram (0.002 mole) of 4-(4-chloro-5-difluoromethoxy-1-methylpyrazol-3-yl)-3-fluorophenol (prepared in Steps D through H of Example 1), 0.32 gram (0.002 mole) of 4-chlorophenylmethyl chloride (commercially available), and 0.41 gram (0.003 mole) of potassium carbonate in 60 mL of N,N-dimethylformamide. The crude reaction product was purified by column chromatography on silica gel, using methylene chloride as the eluant. The product-containing fractions were combined and concentrated under reduced pressure, yielding 0.45 gram of title compound, mp 78–79° C. The NMR spectrum was consistent with the proposed structure.

EXAMPLE 4

Synthesis of 2-[2-[4-(4-chloro-5-difluoromethoxy-1-methyl-pyrazol-3-yl)phenoxymethyl]-5-methylphenoxy]propanoic acid (Compound 49)

A solution of 7.6 grams (0.016 mole) of methyl 2-[2-[4-(4-chloro-5-difluoromethoxy-1-methylpyrazol-3-yl)phenoxymethyl]-5-methylphenoxy]-propanoate (Compound 36—prepared as in Example 2) in 50 mL of methanol was stirred, and a solution of 3.0 grams (0.075 mole) of sodium hydroxide in 30 mL of water was added. Upon completion of addition, the reaction mixture was stirred at ambient temperature for about 18 hours. After this time, the reaction mixture was combined with another, smaller run of this reaction. The combined reaction mixtures were concentrated under reduced pressure to remove the methanol solvent. The aqueous residue was washed with diethyl ether, then made acidic with aqueous 10% hydrochloric acid. The mixture was extracted with three 100 mL portions of ethyl acetate. The combined extracts were dried with magnesium sulfate and filtered. The filtrate was concentrated under reduced pressure to a viscous oil residue. The residue was dried with warming under reduced pressure, yielding 7.5 grams of title compound. The theoretical yield for the combined reaction mixtures was 7.9 grams. The NMR spectrum was consistent with the proposed structure.

EXAMPLE 5

Synthesis of ethyl 2-[2-[4-(4-chloro-5-difluoromethoxy-1-methylpyrazol-3-yl)phenoxymethyl]-5-methylphenoxy]-propanoate (Compound 43)

A stirred solution of 1.6 grams (0.003 mole) of 2-[2-[4-(4-chloro-5-difluoromethoxy-1-methylpyrazol-3-yl)phenoxymethyl]-5-methylphenoxy]-propanoic acid, 0.32 mL (0.004 mole) of ethyl iodide, and 0.49 mL (0.3 mole) of 1,8-diazobicyclo[5.4.0]undec-7-ene (DBU) in 40 mL of acetonitrile was heated at reflux for two hours. The reaction mixture was then cooled and concentrated under reduced pressure to a residue. The residue was taken up in water and extracted with three 60 mL portions of ethyl acetate. The combined extracts were dried with magnesium sulfate and filtered. The filtrate was concentrated under reduced pressure to a residue. The residue was subjected to column chromatography on silica gel, using 3:7 diethyl ether in heptane as the eluant. The product-containing fractions were combined and concentrated under reduced pressure, yielding 0.9 gram of title compound. The NMR spectrum was consistent with the proposed structure.

EXAMPLE 6

Synthesis of 2-[5-ethyl-2-[4-(4-chloro-5-difluoromethoxy-1-methylpyrazol-3-yl)phenoxymethyl]phenoxy]propanamide (Compound 47)

Step A Synthesis of 2-[5-ethyl-2-[4-(4-chloro-5-difluoromethoxy-1-methyl-pyrazol-3-yl)phenoxymethyl]phenoxy]propanoic acid as an intermediate (Compound 51)

This compound was prepared in a manner analogous to that of Example 4, using 12.0 grams (0.024 mole) of methyl 2-[5-ethyl-2-[4-(4-chloro-5-difluoromethoxy-1-methylpyrazol-3-yl)phenoxymethyl]phenoxy]propanoate (Compound 44—prepared as in Example 1), 2.4 grams (0.036 mole) of potassium hydroxide, and 100 mL of water in 100 mL of ethanol. The yield of title compound was 11.1 grams. The NMR spectrum was consistent with the proposed structure.

Step B Synthesis of 2-[5-ethyl-2-[4-(4-chloro-5-difluoromethoxy-1-methyl-pyrazol-3-yl)phenoxymethyl]phenoxy]propanoic acid chloride as an intermediate A solution of 3.5 grams (0.009 mole) of 2-[5-ethyl-2-[4-(4-chloro-5-di-fluoromethoxy-1-methylpyrazol-3-yl)phenoxymethyl]phenoxy]propanoic acid, 1.4 grams (0.011 mole) of oxalyl chloride and one drop (catalyst) of N,N-dimethylformamide in 50 mL of diethyl ether was stirred at ambient temperature for about 18 hours. After this time, the reaction mixture was concentrated under reduced pressure, yielding about 4.9 grams of the title acid chloride. The acid chloride was used without further purification.

Step C Synthesis of 2-[5-ethyl-2-[4-(4-chloro-5-difluoromethoxy-1-methyl-pyrazol-3-yl)phenoxymethyl]phenoxy]propanamide (Compound 47)

A solution of 1.0 gram (0.0019 mole) of 2-[5-ethyl-2-[4-(4-chloro-5-difluoromethoxy-1-methylpyrazol-3-yl)phenoxymethyl]phenoxy]propanoic acid chloride in about 30 mL of methylene chloride is stirred, and gaseous ammonia (excess) is bubbled in during a ten minute period. After this time, the reaction mixture is stirred for about two hours at ambient temperature. The reaction mixture is washed with water and dried with magnesium sulfate. The mixture is filtered, and the filtrate is concentrated under reduced pressure, yielding the title compound.

EXAMPLE 7

Synthesis of N,N-dimethyl-2-[2-[5-ethyl-4-(4-chloro-5-difluoromethoxy-1-methylpyrazol-3-yl)phenoxymethyl]-pheyoxy]propanamide (Compound 55)

A solution of 1.0 gram (0.0019 mole) of 2-[5-ethyl-2-[4-(4-chloro-5-difluoromethoxy-1-methylpyrazol-3-yl)

phenoxymethyl]phenoxy]propanoic acid chloride, 0.24 gram (0.0030 mole) of dimethylamine hydrochloride, and 0.6 mL (0.0040 mole) of triethylamine in 50 mL of diethyl ether was stirred at ambient temperature for about five hours. After this time an additional 0.4 gram of dimethylamine hydrochloride and 0.8 gram of triethylamine were added. The reaction mixture was then stirred at ambient temperature for about 18 hours. After this time the reaction mixture was washed with water and dried with magnesium sulfate. The mixture was filtered and concentrated under reduced pressure to a residue. The residue was subjected to column chromatography on silica gel, using 1:4 to 4:1 mixtures of ethyl acetate in hexane. The product-containing fractions were combined and concentrated under reduced pressure, yielding 0.4 gram of title compound. The NMR spectrum was consistent with the proposed structure.

EXAMPLE 8

Synthesis of N-methylsulfonyl-2-[5-ethyl-2-[3-fluoro-4-(4-chloro-5-difluoromethoxy-1-methylpyrazol-3-yl)-phenoxymethyl]phenoxy] propanamide (Compound 111)

Step A Synthesis of 2-[5-ethyl-2-[3-fluoro-4-(4-chloro-5-difluoromethoxy-1-methylpyrazol-3-yl)phenoxymethyl] phenoxy]propanoic acid as an inter mediate (Compound 102)

This compound is prepared in a manner analogous to that of Example 4, using 12.3 grams (0.024 mole) of methyl 2-[5-ethyl-2-[3-fluoro-4-(4-chloro-5-difluoromethoxy-1-methylpyrazol-3-yl)phenoxymethyl]phenoxy]propanoate (Compound 104—prepared as in Example 1), 2.4 grams (0.036 mole) of potassium hydroxide, and 100 mL of water in 100 mL of ethanol, yielding title compound.

Step B Synthesis of 2-[5-ethyl-2-[3-fluoro-4-(4-chloro-5-difluoromethoxy-1-methylpyrazol-3-yl)phenoxymethyl] phenoxy]propanoic acid chloride as an intermediate This compound is prepared in a manner analogous to that of Step B of Example 6, using 4.5 grams (0.009 mole) of 2-[5-ethyl-2-[3-fluoro-4-(4-chloro-5-di-fluoromethoxy-1-methylpyrazol-3-yl)phenoxymethyl]phenoxy]propanoic acid, 1.4 grams (0.011 mole) of oxallyl chloride and one drop (catalyst) of N,N-dimethylformamide in 50 mL of diethyl ether, yielding the title acid chloride.

Step C Synthesis of N-methylsulfonyl-2-[5-ethyl-2-[3-fluoro-4-(4-chloro-5-difluoromethoxy-1-methylpyrazol-3-yl)phenoxymethyl]phenoxy]propanamide (Compound 11)

A stirring mixture of 2.6 0 grams (0.0050 mole) of 2-[5-ethyl-2-[3-fluoro-4-(4-chloro-5-difluoromethoxy-1-methylpyrazol-3-yl)phenoxymethyl]phenoxy]propanoic acid chloride and 0.52 gram (0.0055 mole) of methylsulfonylamine is heated at about 120° C. for two hours. The reaction mixture is then cooled and dissolved in about 35 mL of methylene chloride. The solution is washed with water, dried with magnesium sulfate, and filtered. The filtrate is concentrated under reduced pressure, yielding the title compound.

EXAMPLE 9

Synthesis of methyl 2-[5-chloro-2-[4-(4-chloro-5-difluoro-methoxy-1-methylpyrazol-3-yl) phenylthiomethyl]-phenoxy]propanoate (Compound 135)

Step A Synthesis of 4-(4-chloro-5-difluoromethoxy-1-methylpyrazol-3-yl)phenylsulfonyl chloride as an intermediate A mixture of 2.1 grams (0.0078 mole) of 3-(4-aminophenyl)-4-chloro-5-difluoro-methoxy-1-methylpyrazole (prepared as in Steps E through H of Example 2) in 20 mL of hydrochloric acid is cooled to 0° C, and 0.6 gram (0.0084 mole) of sodium nitrite in five mL of water is added slowly while maintaining the reaction mixture temperature at 0–5° C. Upon completion of addition, the reaction mixture is stirred at ambient temperature for two hours. During this time, in a separate reaction vessel, a solution of 1.1 grams (0.0080 mole) of copper(II) chloride in five mL of water and 20 mL of acetic acid is prepared, and sulfur dioxide is bubbled through this solution until it is saturated. After having been stirred for two hours, the sodium nitrite/hydrochloric acid reaction mixture is added slowly to the solution saturated with sulfur dioxide. Upon completion of addition, the reaction mixture is stirred for two hours and poured into ice. The resultant precipitate is collected by filtration and dried, yielding the title sulfonyl chloride.

Step B Synthesis of 4-(4-chloro-5-difluoromethoxy-1-methylpyrazol-3-yl)thiophenol as an intermediate Gaseous hydrogen chloride is bubbled into a mixture of 3.3 grams (0.0146 mole) of tin(II) chloride in 40 mL of acetic acid during a five minute period. The resultant solution is heated to 85° C., and a hot solution of 1.7 grams (0.00485 mole) of 4-(4-chloro-5-difluoromethoxy-1-methylpyrazol-3-yl)phenylsulfonyl chloride in 20 mL of acetic acid is added to the first solution. Upon completion of addition, the reaction mixture is stirred at 85° C. for 45 minutes. The reaction mixture is then cooled to ambient temperature and poured into 120 mL of hydrochloric acid. After this, the mixture is stirred with a saturated aqueous sodium chloride solution, then extracted with several portions of ethyl acetate. The combined extracts are washed with water and dried with magnesium sulfate. The mixture is filtered, and the filtrate is concentrated under reduced pressure, yielding the title compound.

Step C Synthesis of methyl 2-[5-chloro-2-[4-(4-chloro-5-difluoromethoxy-1-methylpyrazol-3-yl)phenylthiomethyl] phenoxy]propanoate
(Compound 135)

This compound is prepared in a manner analogous to that of Step I of Example 1, using 0.58 gram (0.002 mole) of 4-(4-chloro-5-difluoromethoxy-1-methylpyrazol-3-yl) thiophenol, 0.32 gram (0.002 mole) of methyl 2-(5-chloro-2-chloromethylphenoxy)propanoate (prepared as in Steps A through D of Example 2), and 0.41 gram (0.003 mole) of potassium carbonate in 60 mil of N,N-di-methylformamide, yielding the title compound.

EXAMPLE 10

Synthesis of 2-(2-methoxyethoxy)ethyl 2-[5-ethyl-2-[3-fluoro-4-(4-chloro-5-difluoromethoxy-1-methylpyrazol-3-yl)phenoxmethyl]phenoxy] propanoate (Compound 106)

A stirring solution of 1.54 grams (0.003 mole) of methyl 2--[5-ethyl-2-[3-fluoro-4-(4-chloro-5-difluoromethoxy-1-methylpyrazol-3-yl)phenoxymethyl]-phenoxy]propanoate (prepared as in Example 1), 0.36 gram (0.003 mole) of 2-(2-methoxyethoxy)ethanol, and 1.08 gram (0.009 mole) of titanium(IV) isopropoxide in toluene is heated at reflux for about 72 hours. The reaction mixture is then concentrated under reduced pressure, yielding the title compound.

EXAMPLE 11

Synthesis of methyl 2-[5-chloro-2-[4-(4-chloro-3-difluoro-methoxy-1-methylpyrazol-5-yl) phenoxymethyl]-phenoxy]propanoate (Compound 143)

Step A Synthesis of 3-(4-methoxyphenyl)-5-hydroxy-1-(1,1-dimethyl-ethyl)pyrazole as an intermediate This compound was prepared in a manner analogous to that of Step E of Example 1, using 22.7 grams (0.102 mole) of ethyl 3-(4-methoxyphenyl)-3-oxopropanoate, 13.4 grams (0.107 mole) of t-butylhydrazine hydrochloride, and 11.4 grams (0.107 mole) of triethylamine in 100 mL of ethanol. The yield of 3-(4-methoxyphenyl)-5-hydroxy-1-(1,1-dimethylethyl)pyrazole was 25.0 grams. The NMR spectrum was consistent with the proposed structure.

Step B Synthesis of 5-difluoromethoxy-3-(4-methoxyphenyl)-1-(1,1-dimethylethyl)pyrazole as an intermediate A solution of 24.0 grams (0.097 mole) of 3-(4-methoxyphenyl)-5-hydroxy-1-(1,1-dimethylethyl)pyrazole in 200 mL of tetrahydrofuran was stirred, and 1.0 gram (catalyst) of 1,4,7,10,13,16-hexaoxacyclooctadecane (18-Crown-6) was added. The mixture was heated to reflux, and chlorodifluoromethane was bubbled through the reaction mixture during a 20 minute period. The reaction mixture was then cooled and made acidic with concentrated hydrochloric acid. The mixture was extracted with three 100 mL portions of ethyl acetate. The combined extracts were dried with magnesium sulfate and filtered. The filtrate was concentrated under reduced pressure to a residue. The residue was subjected to column chromatography on silica gel, using mixtures of ethyl acetate and heptane. The product-containing fractions were combined and concentrated under reduced pressure, yielding 6.2 grams of title compound, mp 56–58° C. The NMR spectrum was consistent with the proposed structure.

Step C Synthesis of 4-chloro-5-difluoromethoxy-3-(4-methoxyphenyl)-1-(1,1-dimethylethyl)pyrazole as an intermediate This compound was prepared in a manner analogous to that of Step G of Example 1, using 5.9 grams (0.020 mole) of 5-difluoromethoxy-3-(4-methoxy-phenyl)-1-(1,1-dimethylethyl)pyrazole and 2.9 grams (0.022 mole) of N-chloro-succinimide in 60 mL of N,N-dimethylformamide. The yield of 4-chloro-5-difluoromethoxy-3-(4-methoxyphenyl)-1-(1,1-dimethylethyl)pyrazole was 6.1 grams, mp 84.5–86° C. The NMR spectrum was consistent with the proposed structure.

Step D Synthesis of a tautomeric mixture of 4-(4-chloro-5-difluoromethoxypyrazol-3-yl)phenol and 4-(4-chloro-3-difluoromethoxypyrazol-3-yl)phenol as an intermediate This compound was prepared in a manner analogous to that of Step H of Example 1, using 5.8 grams (0.017 mole) of 4-chloro-5-difluoromethoxy-3-(4-methoxyphenyl)-1-(1,1-dimethylethyl)pyrazole and 34.8 mL (0.035 mole) of 1M boron tribromide (in methylene chloride) in 60 mL of methylene chloride. The reaction mixture was poured into water and extracted with four portions of methylene chloride. The combined extracts were dried with magnesium sulfate and filtered. The filtrate was concentrated under reduced pressure to a residue. The residue was subjected to column chromatography on silica gel, using methylene chloride, then a 2:3 mixture of ethyl acetate and heptane. The product-containing fractions were combined and concentrated under reduced pressure, yielding 3.1 grams of off-white solid, mp 154–155.5° C. IR, NMR, and Mass Spectral analysis indicated the solid to be a tautomeric mixture of 4-(4-chloro-5-difluoromethoxypyrazol-3-yl) phenol and 4-(4-chloro-3-difluoromethoxypyrazol-3-yl) phenol, rather than the intended 4-[4-chloro-5-difluoromethoxy-1-(1,1-dimethylethyl)pyrazol-3-yl]phenol.

Step E Synthesis of a mixture of 4-chloro-5-difluoromethoxy-3-(4-methoxyphenyl)-1-methylpyrazole and 4-chloro-3-difluoromethoxy-5-(4-methoxyphenyl)-1-methylpyrazole as intermediates A solution of 2.9 grams (0.013 mole) of the tautomeric mixture of 4-(4-chloro-5-difluoromethoxypyrazol-3-yl) phenol and 4-(4-chloro-3-difluoromethoxypyrazol-3-yl) phenol in 20 mL of N,N-dimethylformamide was stirred and 5.4 grams (0.038 mole) of methyl iodide and 5.4 grams (0.038 mole) of potassium carbonate were added. The reaction mixture was then warmed to 60–70° C. where it stirred for two hours. After this time the reaction mixture was diluted with aqueous 10% lithium chloride and extracted with three portions of ethyl acetate. The combined extracts were washed with aqueous 10% lithium chloride, dried with magnesium sulfate, and filtered. The filtrate was concentrated under reduced pressure to a residue. The residue was subjected to column chromatography on silica gel, using 1:4 ethyl acetate and heptane as the eluant. The product-containing fractions were combined and concentrated under reduced pressure, yielding 2.9 grams of the title mixture, mp 55–58° C. NMR spectral analysis indicated the mixture to be 16.6% of the 3-difluoromethoxy isomer and 83.4% of the 5-difluoromethoxy isomer.

Step F Synthesis of a mixture of 4-(4-chloro-5-difluoromethoxy-1-methyl-pyrazol-3-yl)phenol and 4-(4-chloro-3-difluoromethoxy-1-methyl-pyrazol-5-yl)phenol as intermediates This isomeric mixture is prepared in a manner analogous to that of Step H of Example 1, using 2.9 grams (0.013 mole) of a mixture of 4-chloro-5-difluoromethoxy-3-(4-methoxyphenyl)-1-methylpyrazole and 4-chloro-3-difluoromethoxy-5-(4-methoxyphenyl)-1-methylpyrazole and 25.9 mL (0.026 mole) of 1M boron tribromide (in methylene chloride) in 60 mL of methylene chloride. The product obtained is predominantly 4-(4-chloro-3-difluoromethoxy-1-methylpyrazol-5-yl)phenol, which is separated from its isomer by column chromatography.

Step G Synthesis of methyl 2-[5-chloro-2-[4-(4-chloro-3-difluoromethoxy-1-methylpyrazol-5-yl)phenoxymethyl] phenoxy]propanoate (Compound 143)

This compound was prepared in a manner analogous to that of Step I of Example 1, using 0.82 gram (0.0030 mole) of 4-(4-chloro-3-difluoromethoxy-1-methylpyrazol-5-yl) phenol, 0.95 gram (0.0036 mole) of methyl 2-(5-chloro-2-chloromethylphenoxy)propanoate (prepared in Steps A through D of Example 2), and 0.62 gram (0.0045 mole) of potassium carbonate in N,N-dimethylformamide, yielding the title compound.

EXAMPLE 12

Synthesis of methyl 2-[5-methyl-2-[3-fluoro-4-(4-chloro-2,3-dihydro-1-difluoromethyl-2-methyl-3(1 H)-pyrazolon-5-yl)phenoxymethyl]phenoxy] propanoate (Compound 158)

Step A Synthesis of 1-difluoromethyl-2,3-dihydro-5-(2-fluoro-4-methoxyphenyl)-2-methyl-3(1 H)-pyrazolone as an intermediate This compound was prepared in a manner analogous to that of Step F of Example 1, using 36.1 grams (0.162 mole) of 3-(2-fluoro-4-methoxyphenyl)-5-hydroxy-1-methylpyrazole and 67.4 grams (0.487 mole) of potassium carbonate in 200 mL of N,N-dimethylformamide. This reaction differed from Step F of Example 1 in that it was conducted at a temperature of 60–65° C., rather than at 120° C. For this reason the expected reaction product of 5-difluoromethoxy-3-(2-fluoro-4-methoxyphenyl)-1-methylpyrazole was not obtained. NMR spectral analysis of the reaction product indicated it to be 1-difluoromethyl-2,3-dihydro-5-(2-fluoro-4-methoxyphenyl)-2-methyl-3(1 H)-pyrazolone. The yield of this material was about 4.8 grams. This reaction was repeated to yield an additional 19.4 grams of material.

Step B Synthesis of 4-chloro-1-difluoromethyl-5-(2-fluoro-4-methoxy-phenyl)-2-methyl-3-pyrazolone as an intermediate This compound was prepared in a manner analogous to that of Step G of Example 1, using 25.0 grams (0.092 mole) of 1-difluoromethyl-2,3-dihydro-5-(2-fluoro-4-methoxyphenyl)-2-methyl-3(1 H)-pyrazolone and 12.3 grams (0.092 mole) of N-chlorosuccinimide in 120 mL of N,N-dimethylformamide. The yield of title compound was 25.4 grams.

Step C Synthesis of 3-fluoro-4-(4-chloro-1-difluoromethyl-2,3-dihydro-2-methyl-3(1 H)-pyrazolon-5-yl)phenol as an intermediate This compound was prepared in a manner analogous to that of Step H of Example 1, using 25.4 grams (0.083 mole) of 4-chloro-1-difluoromethyl-2,3-dihydro-5-(2-fluoro-4-methoxyphenyl)-2-methyl-3( 1 H)-pyrazolone, 182 mL (0.182 mole) of 1M boron tribromide in 200 mL of methylene chloride. The yield of title compound was 22.1 grams, mp 143–145° C. The NMR spectrum was consistent with the proposed structure.

Step D Synthesis of methyl 2-[5-methyl-2-[3-fluoro-4-(4-chloro-2-difluoro-methyl-1-methylpyrazol-5-on-3-yl) phenoxymethyl]phenoxy]propanoate
(Compd 158)

This compound was prepared in a manner analogous to that of Step I of Example 1, using 1.1 grams (0.004 mole) of 3-fluoro-4-(4-chloro-2-difluoromethyl-1-methylpyrazol-5-on-3-yl)phenol, 1.2 grams (0.005 mole) of methyl 2-(2-chloromethyl-5-methylphenoxy)propanoate (prepared in a manner analogous to Steps A through C of Example 1), and 0.7 gram (0.005 mole) of potassium carbonate in 20 mL of N,N-dimethylformamide. The yield of methyl 2-[5-methyl-2-[3-fluoro-4-(4-chloro-2-difluoromethyl-1-methylpyrazol-5-on-3-yl)phenoxymethyl]phenoxy]propanoate was about 1.0 gram, mp 80–81° C. The NMR spectrum was consistent with the proposed structure.

EXAMPLE 13

Synthesis of methyl 2-[5-ethyl-2-[3-fluoro-4-(4-methoxy-carbonyl-5-trifluoromethylisoxazol-3-yl) phenoxy-methyl]phenoxy]propanoate (Compound 171)

Step A Synthesis of methyl [3-[2-fluoro-4-(1-methylethoxy)phenyl]-5-trifluoromethylisoxazol-4-yl] carboxylate as an intermediate Using the method of H. C. Brown et al. (Synthesis, p 704, 1979), 2-fluoro-5-(1-methylethoxy)benzoic acid is converted to the corresponding benzaldehyde. Then, using thc method of B. C. Hamper et al. (J. Agric. Food Chem. 1995, 43, 219–228), the benzaldehyde is reacted first with hydroxylamine hydrochloride, then with N-chlorosuccinimide, yielding the intermediate 2-fluoro-5-(1-methylethoxy)benzohydroximinoyl chloride. The chloride is in turn cyclized with methyl 4,4,4-trifluoro-2-butynoate in aqueous 5% sodium hydroxide affording the intermediate methyl [3-[2-fluoro-4-(1-methylethoxy) phenyl]-5-trifluoromethylisoxazol-4-yl]carboxylate.

Step B Synthesis of methyl [3-(2-fluoro-4-hydroxyphenyl)-5-trifluoro methylisoxazol-4-yl] carboxylate as an intermediate Concentrated sulfuric acid, 50 mL, is stirred and cooled to about 15 ° C., and 5.0 grams (0.014 mole) of methyl [3-[2-fluoro-4-(1-methylethoxy)phenyl]-5-trifluoromethylisoxazol-4-yl]carboxylate is added portionwise. Upon completion of addition, the reaction mixture is stirred at 15° C. for about 15 minutes, then it is poured into ice-water. The resultant solid is collected by filtration and dried, yielding the title compound.

Step C Synthesis of methyl 2-[5-ethyl-2-[3-fluoro-4-(4-methoxycarbonyl-5-trifluoromethylisoxazol-3-yl] phenoxymethyl]phenoxy]propanoate (Compound 171)

This compound is prepared in a manner analogous to that of Step I of Example 1, using 0.92 gram (0.0030 mole) of methyl [3-(2-fluoro-4-hydroxyphenyl)-5-trifluoromethylisoxazol-4-yl]carboxylate, 0.84 gram (0.0036 mole) of methyl 2-(2-chloromethyl-5-ethyl-phenoxy)propanoate (prepared in Steps A through C of Example 1), and 0.62 gram (0.0045 mole) of potassium carbonate in N,N-dimethylformamide, yielding the title compound.

EXAMPLE 14

Synthesis of methyl 2-[5-ethyl-2-[3-fluoro-4-(4-chloro-5-trifluoromethylisoxazol-3-yl) phenoxymethyl]phenoxy]propanoate (Compound 169)

Step A Synthesis of [3-[2-fluoro-4-(1-methylethoxy) phenyl]-5-trifluoro methylisoxazol-4-yl]carboxylic acid as an intermediate A solution of 1.8 grams (0.045 mole) of sodium hydroxide in 100 mL of water is stirred, and 15.0 grams (0.043 mole) of methyl [3-[2-fluoro-4-(1-methyl-ethoxy)phenyl]-5-trifluoromethylisoxazol-4-yl]carboxylate (prepared as in Step A of Example 13) is added. Upon completion of addition, the reaction mixture is stirred at ambient temperature for about one hour. The reaction mixture is then cooled in an ice-water bath, and made acidic with concentrated hydrochloric acid. The resultant precipitate is collected by filtration and dried, yielding the title carboxylic acid.

Step B Synthesis of 1,1-dimethylethyl N-[3-[2-fluoro-4-(1-methylethoxy)-phenyl]-5-trifluoromethylisoxazol-4-yl] carbamate as an intermediate A stirred mixture of 10.0 grams (0.030 mole) of [3-[2-fluoro-4-(1-methyethoxy)-phenyl]-5-trifluoromethylisoxazol-4-yl]carboxylic acid, 8.3 grams (0.030 mole) of diphenyl-phosphoryl azide, and 3.0 grams (0.030 mole) of triethylamine in 80 mL of t-butanol is heated at reflux for about 18 hours. After this time, the reaction mixture is concentrated under reduced pressure to a residue. The residue is purified by column chromatography, yielding the title compound.

Step C Synthesis of 4-amino-3-[2-fluoro-4-(1,1-dimethylethoxy)phenyl]-5-trifluoro-methylisoxazole as an intermediate Acetic acid, 50 mL, is stirred and cooled to about 0° C., and 10.0 grams (0.026 mole) of 1,1-dimethylethyl N-[3-[2-fluoro-4-(1-methylethoxy)phenyl]-5-trifluoromethyl-isoxazol-4-yl]carbamate is added. Upon completion of addition, the reaction mixture is allowed to warm to ambient temperature where it stirred for about 90 minutes. The reaction mixture is then stirred with water and diethyl ether and made basic with sodium bicarbonate. The organic phase is separated and dried with magnesium sulfate. The mixture is filtered, and the filtrate is concentrated under reduced pressure to a residue. The residue is purified using column chromatography, yielding the title compound.

Step D Synthesis of 4-chloro-3-[2-fluoro-4-(1,1-dimethylethoxy)phenyl]-5-trifluoro-methylisoxazole as an intermediate Using the method of M. P. Doyle et al. (J. Org. Chem., Vol 42, No. 14, 1977), 4-amino-3-[2-fluoro-4-(1,1-dimethylethoxy)phenyl]-5-trifluoromethylisoxazole is treated with anhydrous copper(II) chloride, and t-butyl nitrite in anhydrous acetonitrile, yielding the corresponding 4-chloro-3-[2-fluoro-4-(1,1-dimethylethoxy)phenyl]-5-trifluoromethyl-isoxazole.

Step E Synthesis of 3-fluoro-4-(4-chloro-5-trifluoromethylisoxazol-3-yl)phenol as an intermediate This compound is prepared in a manner analogous to that of Step H of Example 1, using 3.2 grams (0.010 mole) of 4-chloro-3-[2-fluoro-4-(1,1-dimethylethoxy)phenyl]-5-trifluoromethylisoxazole and 20 mL (0.020 mole) of 1M boron tribromide (in methylene chloride) in 50 mL of methylene chloride, yielding 3-fluoro-4-(4-chloro-5-trifluoromethyl-isoxazol-3-yl)phenol.

Step F Synthesis of methyl 2-[5-ethyl-2-(3-fluoro-4-(4-chloro-5-trifluoro methylisoxazol-3-yl]phenoxymethyl] phenoxy]propanoate
(Compound 169)

This compound is prepared in a manner analogous to that of Step I of Example 1, using 0.84 gram (0.0030 mole) of 3-fluoro-4-(4-chloro-5-trifluoromethylisoxazol-3-yl)phenol, 0.84 gram (0.0036 mole) of methyl 2-(2-chloromethyl-5-ethylphenoxy)propanoate (prepared in Steps A through C of Example 1), and 0.62 gram (0.0045 mole) of potassium carbonate in N,N-dimethylformamide, yielding the title compound.

EXAMPLE 15

Synthesis of methyl 2-[5-ethyl-2-[4-[5-chloro-1-(1-methylethyl)-2-methylimidazol-4-yl] phenoxymethyl]phenoxy]propanoate (Compound 176)

Step A Synthesis of 4-(4-methoxyphenyl)-2-methylimidazol-5-one as an intermediate A stirred mixture of 11.8 grams (0.10 mole) of acetamidine hydrochloride in 200 mL of tetrahydrofuran is cooled to about 15° C., and 41.8 grams (0.30 mole) of potassium carbonate is added portionwise. To this is then added portionwise 21.8 grams (0.10 mole) of 2-chloro-2-(4-methoxyphenyl)acetyl chloride. Upon completion of addition, the reaction mixture is stirred for 15 minutes at 15° C., then it is warmed to reflux where it stirred for about four hours. The reaction mixture is then cooled and filtered to collect the by-product potassium chloride. The filtrate is concentrated under reduced pressure, yielding 4-(4-methoxyphenyl)-2-methylimidazol-5-one.

Step B Synthesis of 5-chloro-4-(4-methoxyphenyl)-2-methylimidazole as an intermediate A stirred solution of 10.0 grams (0.049 mole) of 4-(4-methoxyphenyl)-2-methyl-imidazol-5-one in 50 mL of phosphorous oxychloride is heated at reflux for about three hours. After this time, the reaction mixture is concentrated under reduced pressure, yielding 5-chloro-4-(4-methoxyphenyl)-2-methylimidazole.

Step C Synthesis of 5-chloro-1-(1-methylethyl)-4-(4-methoxyphenyl)-2-methyl-imidazole as an intermediate A mixture of 8.9 grams (0.04 mole) of 5-chloro-4-(4-methoxyphenyl)-2-methyl-imidazole, 34.0 grams (0.20 mole) of isopropyl iodide, and 27.8 grams (0.02 mole) of potassium carbonate in 200 mL of acetone is stirred at ambient temperature for about 18 hours. After this time the reaction mixture is shaken with 100 mL of water and 100 mL of diethyl ether. The organic layer is separated, washed with water, and dried with magnesium sulfate. The mixture is filtered and the filtrate is concentrated under reduced pressure to a residue. The residue is purified with column chromatography, yielding 5-chloro-1-(1-methylethyl)-4-(4-methoxyphenyl)-2-methylimidazole.

Step D Synthesis of 4-[5-chloro-1-(1-methylethyl)-2-methylimidazol-4-yl]phenol as an intermediate This compound is prepared in a manner analogous to that of Step H of Example 1, using 2.6 grams (0.010 mole) of 5-chloro-1-(1-methylethyl)-4-(4-methoxyphenyl)-2-methylimidazole and 20 mL (0.020 mole) of 1M boron tribromide (in methylene chloride) in 50 mL of methylene chloride, yielding 4-[5-chloro-1-(1-methylethyl)-2-methylimidazol-4-yl]phenol.

Step E Synthesis of methyl 2-[5-ethyl-2-[4-[5-chloro-1-(1-methylethyl)-2-methyl-imidazol-4-yl]phenoxymethyl] phenoxy]propanoate (Compound 176)

This compound is prepared in a manner analogous to that of Step I of Example 1, using 0.75 gram (0.0030 mole) of 4-[5-chloro-1-(1-methylethyl)-2-methylimidazol-4-yl] phenol, 0.84 gram (0.0036 mole) of methyl 2-(2-chlormethyl-5-ethylphenoxy)propanoate (prepared in Steps A through C of Example 1), and 0.62 gram (0.0045 mole) of potassium carbonate in N,N-dimethylformamide, yielding the title compound.

Representative compounds of formula I are shown below in Table 1.

TABLE 1

Herbicidal 1,2,3-trisubstituted-4-[4-(substituted phenylmethoxy or methylthio)phenyl]pyrazoles

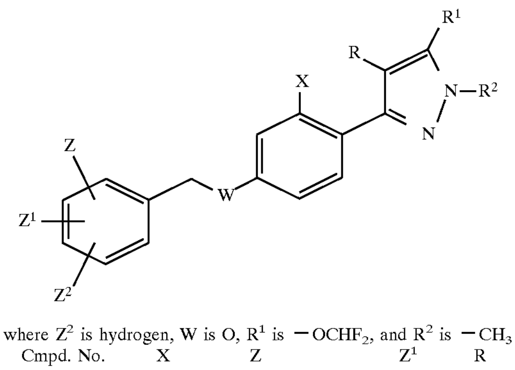

where $Z^2$ is hydrogen, W is O, $R^1$ is $-OCHF_2$, and $R^2$ is $-CH_3$

| Cmpd. No. | X | Z | $Z^1$ | R |
|---|---|---|---|---|
| 1 | H | H | H | Cl |
| 2 | H | H | H | Br |
| 3 | H | 2-Cl | H | Cl |

TABLE 1-continued

| | | | | |
|---|---|---|---|---|
| 4 | H | 2-Cl | 4-Cl | Cl |
| 5 | H | 3-Cl | H | Cl |
| 6 | H | 4-Cl | H | Cl |
| 7 | H | 4-Cl | H | Br |
| 8 | H | 4-Br | H | Cl |
| 9 | H | 4-F | H | Cl |
| 10 | H | $4-CH_3$ | H | Cl |
| 11 | H | $4-CH(CH_3)_2$ | H | Cl |
| 12 | H | $4-OCH_3$ | H | Cl |
| 13 | H | $2-OCH_3$ | 4-Cl | Cl |
| 14 | H | $4-CF_3$ | H | Cl |
| 15 | H | $4-OCHF_2$ | H | Cl |
| 16 | H | $4-NO_2$ | H | Cl |
| 17 | H | 4-CN | H | Cl |
| 18 | Cl | 4-Cl | H | Cl |
| 19 | F | H | H | Cl |
| 20 | F | 4-Cl | H | Cl |
| 21 | F | 4-Br | H | Cl |
| 22 | F | 4-F | H | Cl |
| 23 | F | $4-CH_3$ | H | Cl |
| 24 | F | $4-CH(CH_3)_2$ | H | Cl |
| 25 | F | $4-OCH_3$ | H | Cl |
| 26 | F | $2-OCH_3$ | 4-Cl | Cl |
| 27 | F | $4-OCHF_2$ | H | Cl |
| 28 | F | 4-CN | H | Cl |
| 29 | $-CH_3$ | 4-Cl | H | Cl |

where W is O, $R^1$ is $-OCHF_2$, $R^2$ is $-CH_3$, and $Z^2$ is 2-OA, wherein A is

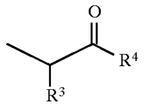

| Cmpd. No. | X | Z | $Z^1$ | R | $R^3$ | $R^4$ |
|---|---|---|---|---|---|---|
| 30 | H | H | H | Cl | H | $-OCH_3$ |
| 31 | H | H | H | Cl | $-CH_3$ | $-OCH_3$ |
| 32 | H | 4-Cl | H | Cl | $-CH_3$ | $-OCH_3$ |
| 33 | H | 4-Cl | H | Cl | $-CH_3$ | $-NH_2$ |
| 34 | H | 4-Cl | H | Cl | $-CH_3$ | $-NHCH_3$ |
| 35 | H | 4-Cl | 3-Cl | Cl | $-CH_3$ | $-OCH_3$ |
| 36 | H | $4-CH_3$ | H | Cl | $-CH_3$ | $-OCH_3$ |
| 37 | H | $4-CH_3$ | H | Br | $-CH_3$ | $-OCH_3$ |
| 38 | H | $4-CH_3$ | H | Cl | $-CH_3$ | $-OCH(CH_3)_2$ |
| 39 | H | $4-CH_3$ | H | Cl | $-CH_3$ | $-O(CH_2)_2O(CH_2)_2OCH_3$ |
| 40 | H | $4-CH_3$ | H | Cl | $-CH_3$ | $-OCH_2CCl_3$ |
| 41 | H | $4-CH_3$ | H | Cl | $-CH_3$ | $-NH_2$ |
| 42 | H | $4-CH_3$ | H | Cl | $-CH_3$ | $-NHCH_3$ |
| 43 | H | $4-CH_3$ | H | Cl | $-CH_3$ | $-OC_2H_5$ |
| 44 | H | $4-C_2H_5$ | H | Cl | $-CH_3$ | $-OCH_3$ |
| 45 | H | $4-C_2H_5$ | H | Cl | $-CH_3$ | $-O(CH_2)_2O(CH_2)_2OCH_3$ |
| 46 | H | $4-C_2H_5$ | H | Cl | $-CH_3$ | $-OCH_2CCl_3$ |
| 47 | H | $4-C_2H_5$ | H | Cl | $-CH_3$ | $-NH_2$ |
| 48 | H | $4-CH_3$ | H | Cl | $-CH_3$ | $-OCH(CH_3)_2$ |
| 49 | H | $4-CH_3$ | H | Cl | $-CH_3$ | $-OH$ |
| 50 | H | 4-phenyl | H | Cl | $-CH_3$ | $-OCH_3$ |
| 51 | H | $4-C_2H_5$ | H | Cl | $-CH_3$ | $-OH$ |
| 52 | H | $4-C_2H_5$ | H | Cl | $-CH_3$ | $-NHOCH_3$ |
| 53 | H | $4-C_2H_5$ | H | Cl | $-CH_3$ | $-ONa$ |
| 54 | H | $4-C_2H_5$ | H | Cl | $-CH_3$ | $-NHCH_3$ |
| 55 | H | $4-C_2H_5$ | H | Cl | $-CH_3$ | $-N(CH_3)_2$ |
| 56 | H | $4-C_3H_7$ | H | Cl | $-CH_3$ | $-OCH_3$ |
| 57 | H | $4-OCH_3$ | H | Cl | $-CH_3$ | $-OCH_3$ |
| 58 | Cl | H | H | Cl | $-CH_3$ | $-OCH_3$ |
| 59 | Cl | H | H | Cl | $-CH_3$ | $-O(CH_2)_2O(CH_2)_2OCH_3$ |
| 60 | Cl | 3-Cl | H | Cl | $-CH_3$ | $-OCH_3$ |
| 61 | Cl | 4-Cl | H | Cl | H | $-OCH_3$ |
| 62 | Cl | 4-Cl | H | Cl | $-CH_3$ | $-OCH_3$ |
| 63 | Cl | 4-Br | H | Cl | $-CH_3$ | $-OCH_3$ |
| 64 | Cl | 4-F | H | Cl | $-CH_3$ | $-OCH_3$ |
| 65 | Cl | 3-Cl | 4-Cl | Cl | $-CH_3$ | $-OCH_3$ |
| 66 | Cl | 3-F | 4-F | Cl | $-CH_3$ | $-OCH_3$ |
| 67 | Cl | $4-CH_3$ | H | Cl | H | $-OCH_3$ |
| 68 | Cl | $4-CH_3$ | H | Cl | $-CH_3$ | $-OCH_3$ |
| 69 | Cl | $4-C_2H_5$ | H | Cl | $-CH_3$ | $-OCH_3$ |
| 70 | F | H | H | Cl | H | $-OCH_3$ |
| 71 | F | H | H | Cl | $-CH_3$ | $-OH$ |
| 72 | F | H | H | Cl | $-CH_3$ | $-OCH_3$ |
| 73 | F | 3-Cl | H | Cl | $-CH_3$ | $-OCH_3$ |
| 74 | F | 4-Cl | H | Cl | H | $-OCH_3$ |
| 75 | F | 4-Cl | H | Cl | $-CH_3$ | $-OH$ |
| 76 | F | 4-Cl | H | Cl | $-CH_3$ | $-OCH_3$ |
| 77 | F | 4-Cl | H | Cl | $-CH_3$ | $-OCH_2CCl_3$ |
| 78 | F | 4-Cl | H | Cl | $-CH_3$ | $-NH_2$ |
| 79 | F | 4-Cl | H | Cl | $-CH_3$ | $-NHCH_3$ |
| 80 | F | 4-Cl | H | Cl | $-CH_3$ | $-N(CH_3)_2$ |
| 81 | F | 5-Cl | H | Cl | $-CH_3$ | $-OCH_3$ |
| 82 | F | 4-Br | H | Cl | $-CH_3$ | $-OCH_3$ |
| 83 | F | 3-Cl | 4-Cl | Cl | $-CH_3$ | $-OCH_3$ |
| 84 | F | 4-Cl | 6-Cl | Cl | $-CH_3$ | $-OCH_3$ |
| 85 | F | 3-F | 4-F | Cl | $-CH_3$ | $-OCH_3$ |
| 86 | F | $4-CH_3$ | H | Cl | H | OH |
| 87 | F | $4-CH_3$ | H | Cl | H | $-OCH_3$ |
| 88 | F | $4-CH_3$ | H | Cl | $-CH_3$ | $-OH$ |
| 89 | F | $4-CH_3$ | H | Cl | $-CH_3$ | $-OCH_3$ |
| 90 | F | $4-CH_3$ | H | Cl | $-CH_3$ | $-OC_2H_5$ |
| 91 | F | $4-CH_3$ | H | Cl | $-CH_3$ | $-OCH(CH_3)_2$ |
| 92 | F | $4-CH_3$ | H | Cl | $-CH_3$ | $-OCH_2CCl_3$ |
| 93 | F | $4-CH_3$ | H | Cl | $-CH_3$ | $-NH_2$ |
| 94 | F | $4-CH_3$ | H | Cl | $-CH_3$ | $-NHC_2H_5$ |
| 95 | F | $4-CH_3$ | H | Cl | $-CH_3$ | $-NHC_3H_7$ |
| 96 | F | $4-CH_3$ | H | Cl | $-CH_3$ | $-NHOCH_3$ |
| 97 | F | $4-CH_3$ | H | Cl | $-CH_3$ | $-NHSO_2CH_3$ |
| 98 | F | $4-CH_3$ | H | Cl | $-CH_3$ | $-N(CH_3)SO_2CH_3$ |
| 99 | F | $4-CH_3$ | H | Cl | $-CH_3$ | $-ONa$ |
| 100 | F | $4-CH_3$ | H | Br | $-CH_3$ | $-OCH_3$ |
| 101 | F | $4-C_2H_5$ | H | Cl | H | $-OCH_3$ |
| 102 | F | $4-C_2H_5$ | H | Cl | $-CH_3$ | $-OH$ |
| 103 | F | $4-C_2H_5$ | H | Cl | $-CH_3$ | $-OCH_3$ |
| 104 | F | $4-C_2H_5$ | H | Cl | $-CH_3$ | $-OCH_2CCl_3$ |
| 105 | F | $4-C_2H_5$ | H | Cl | $-CH_3$ | $-OCH(CH_3)CH_2OCH_3$ |
| 106 | F | $4-C_2H_5$ | H | Cl | $-CH_3$ | $-O(CH_2)_2O(CH_2)_2OCH_3$ |
| 107 | F | $4-C_2H_5$ | H | Cl | $-CH_3$ | $-NH_2$ |
| 108 | F | $4-C_2H_5$ | H | Cl | $-CH_3$ | $-NHCH_3$ |
| 109 | F | $4-C_2H_5$ | H | Cl | $-CH_3$ | $-NHOCH_3$ |
| 110 | F | $4-C_2H_5$ | H | Cl | $-CH_3$ | $-N(CH_3)_2$ |
| 111 | F | $4-C_2H_5$ | H | Cl | $-CH_3$ | $-NHSO_2CH_3$ |
| 112 | F | $4-C_2H_5$ | H | Cl | $-CH_3$ | $-N(CH_3)SO_2CH_3$ |
| 113 | F | $4-C_2H_5$ | H | Cl | $-CH_3$ | $-ONa$ |
| 114 | F | $4-C_3H_7$ | H | Cl | $-CH_3$ | $-OCH_3$ |
| 115 | F | $4-CH(CH_3)_2$ | H | Cl | $-CH_3$ | $-OCH_3$ |
| 116 | F | $4-C_4H_9$ | H | Cl | $-CH_3$ | $-OCH_3$ |
| 117 | F | $4-C(CH_3)_3$ | H | Cl | $-CH_3$ | $-OCH_3$ |
| 118 | F | $4-C(CH_3)_3$ | H | Cl | $-CH_3$ | $-O(CH_2)_2O(CH_2)_2OCH_3$ |
| 119 | F | $5-OCH_3$ | H | Cl | $-CH_3$ | $-OCH_3$ |
| 120 | F | $3,4-(CH_2)_4-$ | | Cl | $-CH_3$ | $-OCH_3$ |
| 121 | F | 4-phenyl | H | Cl | $-CH_3$ | $-OCH_3$ |

where W is O, $Z^1$ is hydrogen, R is Cl, and $Z^2$ is 2-OA, wherein A is

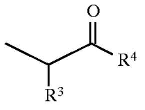

where $R^3$ is $-CH_3$ and $R^4$ is $-OCH_3$

| Cmpd. No. | X | Z | $R^1$ | $R^2$ |
|---|---|---|---|---|
| 122 | F | 4-Cl | $-SCH_3$ | $-CH_3$ |
| 123 | H | $4-CH_3$ | $-SCH_3$ | $-CHF_2$ |
| 124 | F | $4-CH_3$ | $-SCH_3$ | $-CH_3$ |
| 125 | F | $4-CH_3$ | $-SCH_3$ | $-CHF_2$ |
| 126 | F | $4-CH_3$ | $-SOCH_3$ | $-CH_3$ |
| 127 | F | $4-C_2H_5$ | $-SCH_3$ | $-CH_3$ |

TABLE 1-continued where W is O, Z and $Z^1$ are hydrogen, R is Cl, $R^1$ is $-OCHF_2$, $R^2$ is $-CH_3$, and $Z^2$ is 3-OA, wherein A is

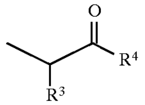

where $R^3$ is $-CH_3$

| Cmpd. No. | X | $R^4$ |
|---|---|---|
| 128 | H | $-OCH_3$ |
| 129 | F | $-OH$ |
| 130 | F | $-OCH_3$ |

where W is O, Z and $Z^1$ are hydrogen, R is Cl, $R^1$ is $-OCHF_2$, $R^2$ is $-CH_3$, and $Z^2$ is 4-OA, wherein A is

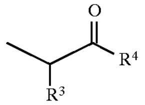

where $R^3$ is $-CH_3$

| Cmpd. No. | X | $R^4$ |
|---|---|---|
| 131 | H | $-OCH_3$ |
| 132 | Cl | $-OCH_3$ |
| 133 | F | $-OCH_3$ |
| 134 | F | $-O(CH_2)_2O(CH_2)_2OCH_3$ |

where W is S, $Z^1$ is hydrogen, R is Cl, $R^1$ is $-OCHF_2$, $R^2$ is $-CH_3$, and $Z^2$ is 2-OA, wherein A is

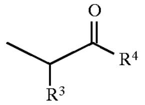

where $R^3$ is $-CH_3$ and $R^4$ is $-OCH_3$

| Cmpd. No. | X | Z |
|---|---|---|
| 135 | H | 4-Cl |
| 136 | H | $4-CH_3$ |
| 137 | H | $4-C_2H_5$ |
| 138 | F | 4-Cl |
| 139 | F | $4-CH_3$ |
| 140 | F | $4-C_2H_5$ |

Herbicidal Compounds Related to 1,2,3-trisubstituted-4-[4-(substitued phenylmethoxy or methylthio)phenyl]pyrazoles

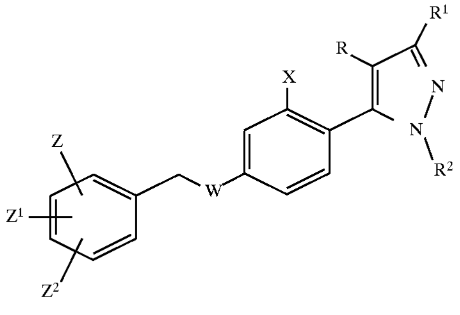

where $Z^2$ is hydrogen, $R^1$ is $-OCHF_2$, W is O, and $R^2$ is $-CH_3$

| Cmpd. No. | X | Z | $Z^1$ | R |
|---|---|---|---|---|
| 141 | H | 4-Cl | H | Cl |
| 142 | F | 4-Cl | H | Cl |

where W is O, $Z^1$ is hydrogen, $R^2$ is $-CH_3$, and $Z^2$ is 2-OA, wherein A is TABLE 1-continued

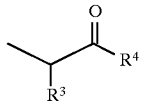

where $R^3$ is $-CH_3$ and $R^4$ is $-OCH_3$

| Cmpd. No. | X | Z | R | $R^1$ |
|---|---|---|---|---|
| 143 | H | 4-Cl | Cl | $-OCHF_2$ |
| 144 | H | $4-CH_3$ | Cl | $-OCHF_2$ |
| 145 | H | $4-C_2H_5$ | Cl | $-OCHF_2$ |
| 146 | H | $4-CH_3$ | Cl | $-CF_3$ |
| 147 | H | $4-CH_3$ | Br | $-OCHF_2$ |
| 148 | F | 4-Cl | Cl | $-OCHF_2$ |
| 149 | F | $4-CH_3$ | Cl | $-OCHF_2$ |
| 150 | F | $4-C_2H_5$ | Cl | $-OCHF_2$ |

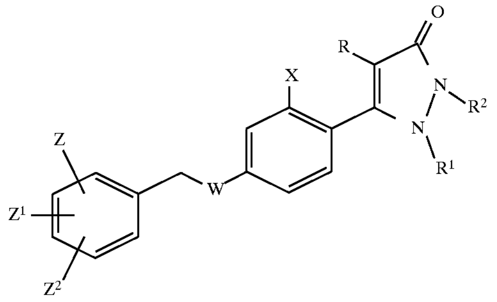

where $Z^1$ and $Z^2$ are hydrogen, Z is 4-Cl, $R^1$ is $-CHF_2$, and $R^2$ is $-CH_3$

| Cmpd. No. | X | R |
|---|---|---|
| 151 | H | Cl |
| 152 | H | Br |
| 153 | F | Cl |

where W is O, $Z^1$ is hydrogen, R is Cl, and $Z^2$ is 2-OA, wherein A is

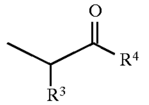

where $R^3$ is $-CH_3$ and $R^4$ is $-OCH3$

| Cmpd. No. | X | Z |
|---|---|---|
| 154 | H | 4-Cl |
| 155 | H | $4-CH_3$ |
| 156 | H | $4-C_2H_5$ |
| 157 | F | 4-Cl |
| 158 | F | $4-CH_3$ |
| 159 | F | $4-C_2H_5$ |

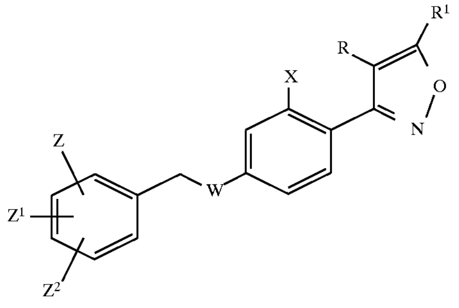

where is $Z^1$ and $Z^2$ are hydrogen, W is O, and $R^1$ is $-CF_3$

TABLE 1-continued

| Cmpd. No. | X | Z | R |
|---|---|---|---|
| 160 | H | 4-Cl | Cl |
| 161 | H | 4-Cl | $-CO_2CH_3$ |
| 162 | F | 4-Cl | Cl |

where W is O, $Z^1$ is hydrogen, $R^1$ is $-CF_3$, and $Z^2$ is 2-OA, wherein A is

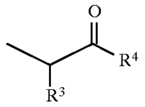

where $R^3$ is $-CH_3$ and $R^4$ is $-OCH_3$

| Cmpd. No. | X | Z | R |
|---|---|---|---|
| 163 | H | 4-Cl | Cl |
| 164 | H | $4-C_2H_5$ | Cl |
| 165 | H | $4-C_2H_5$ | Br |
| 166 | H | $4-CH_3$ | $-CO_2CH_3$ |
| 167 | H | $4-C_2H_5$ | $-CO_2CH_3$ |
| 168 | F | $4-CH_3$ | Cl |
| 169 | F | $4-C_2H_5$ | Cl |
| 170 | F | $4-C_2H_5$ | Br |
| 171 | F | $4-C_2H_5$ | $-CO_2CH_3$ |

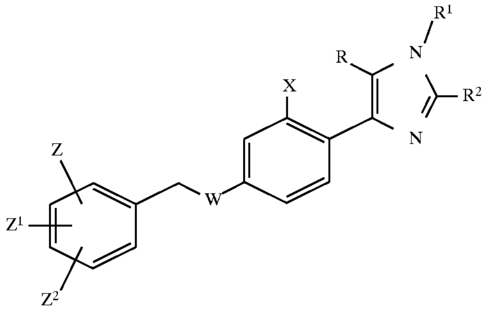

where $Z^1$ and $Z^2$ are hydrogen, W is O, and $R^2$ is $-CH_3$

| Cmpd. No. | X | Z | R | $R^1$ |
|---|---|---|---|---|
| 172 | H | 4-Cl | Cl | $-CHF_2$ |
| 173 | F | 4-Cl | Cl | $-CHF_2$ |

where W is O, $Z^1$ is hydrogen, $R^2$ is $-CH_3$, and $Z^2$ is 2-OA, wherein A is

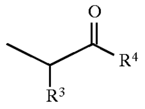

where $R^3$ is $-CH_3$ and $R^4$ is $-OCH_3$

| Cmpd. No. | X | Z | R | $R^1$ |
|---|---|---|---|---|
| 174 | H | $4-C_2H_5$ | Cl | $-CF_2CF_2H$ |
| 175 | H | $4-CH_3$ | Cl | $-CH_3$ |
| 176 | H | $4-C_2H_5$ | Cl | $-CH(CH_3)_2$ |
| 177 | H | $4-CH_3$ | Br | $-CHF_2$ |
| 178 | H | $4-C_2H_5$ | Br | $-CHF_2$ |
| 179 | F | $4-CH_3$ | Cl | $-CHF_2$ |
| 180 | F | $4-C_2H_5$ | Cl | $-CHF_2$ |

Herbicidal 1,2,3-trisubstituted-4-[4-(substituted phenylmethoxy or methylthio)phenyl]pyrazoles TABLE 1-continued

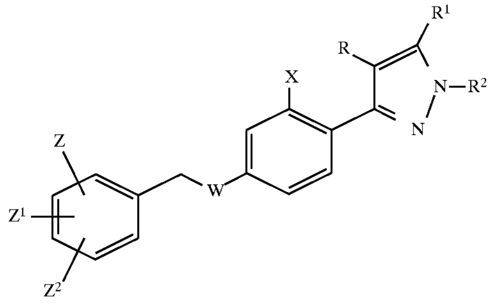

where W is O, $R^1$ is $-OCHF_2$, $R^2$ is $-CH_3$, and $Z^2$ is 2-OA, wherein A is

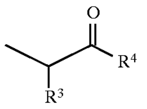

| Cmpd. No. | X | Z | $Z^1$ | R | $R^3$ | $R^4$ |
|---|---|---|---|---|---|---|
| 181 | H | $4-C_2H_5$ | H | Cl | H | $-OH$ |
| 182 | H | $4-C_2H_5$ | H | Cl | H | $-OCH_3$ |
| 183 | H | 4-Br | H | Br | $-CH_3$ | $-OCH_3$ |
| 184 | H | $5-C_2H_5$ | H | Cl | $-CH_3$ | $-OCH_3$ |
| 185 | H | $4-CH_3$ | H | Cl | $-CH_3$ | $-OCH(CH_3)CO_2CH_3$ |
| 186 | H | 4-Cl | H | Br | $-CH_3$ | $-OCH_3$ |
| 187 | H | $3-C_2H_5$ | H | Cl | $-CH_3$ | $-OCH_3$ |
| 188 | H | $4-CH_3$ | H | Cl | $-CH_3$ | ONa |
| 189 | H | $4-CH_3$ | H | Cl | $-CH_3$ | $-N(CH_3)_2$ |
| 190 | H | $4-OC_6H_5$ | H | Cl | $-CH_3$ | $-OCH_3$ |
| 191 | F | $4-CH_3$ | H | Cl | $-CH_3$ | $-OCH(CH_3)CO_2CH_3$ |
| 192 | F | $4-CH_3$ | H | Cl | $-CH_3$ | $-NHCH_3$ |
| 193 | F | $4-CH_3$ | H | Cl | $-CH_3$ | $-N(CH_3)_2$ |
| 194 | F | $5-C_2H_5$ | H | Cl | $-CH_3$ | $-OCH_3$ |

HERBICIDAL ACTIVITY

The optionally substituted phenylmethoxy or phenylmethylthio pyrazole herbicides of the present invention were tested for pre- and post-emergence herbicidal activity against a variety of crops and weeds. The test plants included soybean (*Glycine max*__var. Winchester), field corn (*Zea mays* var. Pioneer 3732), wheat (*Triticum aesticam* var. Lew), morning glory (*Ipomea lacunosa* or *Ipomea hederacea*), velvetleaf (*Abutilon theophrasti*), green foxtail (*Setaria viridis*), Johnsongrass (*Sorghum halepense*), blackgrass (*Aloepecurus myosuroides*), common chickweed (*Stellaria media*), and common cocklebur (*Xanthium strumarium* L.).

For preemergence testing, two disposable fiber flats (8 cm×15 cm×25 cm) for each rate of application of each candidate herbicide were filled to an approximate depth of 6.5 cm with steam-sterilized sandy loam soil. The soil was leveled and impressed with a template to provide five evenly spaced furrows 13 cm long and 0.5 cm deep in each flat. Seeds of soybean, wheat, corn, green foxtail, and johnsongrass were planted in the furrows of the first flat, and seeds of velvetleaf, morningglory, common chickweed, cocklebur, and blackgrass were planted in the furrows of the second flat. The five-row template was employed to firmly press the seeds into place. A topping soil of equal portions of sand and sandy loam soil was placed uniformly on top of each flat to a depth of approximately 0.5 cm. Flats for postemergence testing were prepared in the same manner except that they were planted 9–14 days prior to the preemergence flats and were placed in a greenhouse and watered, thus allowing the seeds to germinate and the foliage to develop.

In both pre- and postemergence tests, a stock solution of the candidate herbicide was prepared by dissolving 0.27 g of the compound in 20 mL of water/acetone (50/50) containing 0.5% v/v sorbitan monolaurate. For an application rate of 3000 g/ha of herbicide a 10 mL portion of the stock solution was diluted with water/acetone (50/50) to 45 mL. The volumes of stock solution and diluent used to prepare solutions for lower application rates are shown in the following table:

| Application Rate (g/ha) | Volume of Stock Solution (mL) | Volume of Acetone/Water (mL) | Total Volume of Spray Solution (mL) |
|---|---|---|---|
| 3000 | 10 | 35 | 45 |
| 1000 | 3 | 42 | 45 |
| 300 | 1 | 44 | 45 |
| 100 | 0.3 | 45 | 45.3 |
| 30 | 0.1 | 45 | 45.1 |
| 10 | 0.03 | 45 | 45.03 |
| 3 | 0.01 | 45 | 45.01 |

The preemergence flats were initially subjected to a light water spray. The four flats were placed two by two along a conveyor belt (i.e., the two preemergence followed by the two postemergence flats). The conveyor belt fed under a spray nozzle mounted about ten inches above the postemergent foliage. The preemergent flats were elevated on the belt so that the soil surface was at the same level below the spray nozzle as the foliage canopy of the postemergent plants. The spray of herbicidal solution was commenced and once stabilized, the flats were passed under the spray at a speed to receive a coverage equivalent of 1000 L/ha. At this coverage the application rates are those shown in the above table for the individual herbicidal solutions. The preemergence flats were watered immediately thereafter, placed in the greenhouse and watered regularly at the soil surface. The postemergence flats were immediately placed in the greenhouse and not watered until 24 hours after treatment with the test solution. Thereafter they were regularly watered at ground level. After 12–17 days the plants were examined and the phytotoxicity data were recorded.

Herbicidal activity data at selected application rates are given for various compounds of the present invention in Tables 2 and 3. The test compounds are identified by numbers which correspond to those in Table 1.

Phytotoxicity data are taken as percent control. Percent control is determined by a method similar to the 0 to 100 rating system disclosed in "Research Methods in Weed Science," 2nd ed., B. Truelove, Ed.; Southern Weed Science Society; Auburn Auburn, Ala., 1977. The rating system is as follows:

| Rating (% Control) | Description of Main Categories | Crop Description | Weed Description |
|---|---|---|---|
| 0 | No Effect | No crop reduction or injury | No weed control |
| 10 | Slight Effect | Slight discoloration or stunting | Very poor weed control |
| 20 | | Some discoloration, stunting or stand loss | Poor weed control |
| 30 | | Crop injury more pronounced, but not lasting | Poor to deficient weed control |
| 40 | Moderate Effect | Moderate injury, crop usually recovers | Deficient weed control |
| 50 | | Crop injury more lasting, recovery doubtful | Deficient to moderate weed control |
| 60 | | Lasting crop injury, no recovery | Moderate weed control |
| 70 | Severe | Heavy injury and stand loss | Control somewhat less than satisfactory |
| 80 | | Crop nearly destroyed, a few survivors | Satisfactory to good weed control |
| 90 | | Only occasional live plants left | Very good to excellent control |
| 100 | Complete Effect | Complete crop destruction | Complete weed destruction |

TABLE 1

| PREEMERGENCE HERBICIDAL ACTIVITY (% CONTROL AT 0.3 kg/ha)) | | | | | | | | | | | | |
|---|---|---|---|---|---|---|---|---|---|---|---|---|
| Cmpd. No. | 1 | 2 | 6 | 7 | 8 | 9 | 19 | 20 | 31 | 32 | 35 | 36 |
| Species | | | | | | | | | | | | |
| Soybean | 0 | 0 | 0 | 0 | 0 | 0 | 0 | 0 | 0 | 15 | 0 | 15 |
| Wheat | 0 | 0 | 0 | 0 | 5 | 0 | 0 | 0 | 0 | 0 | 10 | 10 |
| Corn | 0 | 0 | 20 | 0 | 0 | 0 | 0 | 0 | 0 | 10 | 0 | 20 |
| Velvetleaf | 15 | 0 | 40 | 5 | 30 | 20 | 95 | 95 | 100 | 100 | 50 | 100 |
| Morningglory | 15 | 0 | 20 | 10 | 10 | 20 | 100 | 100 | 90 | 100 | 50 | 100 |
| Chickweed | 75 | 0 | 60 | 10 | 0 | 40 | 100 | 100 | 100 | 100 | 90 | 100 |
| Cocklebur | 0 | 0 | 40 | 0 | 0 | 40 | 0 | 20 | 20 | 70 | 0 | 30 |
| Blackgrass | ND | 0 | ND | 10 | 0 | ND | ND | 60 | 30 | ND | 0 | ND |
| Green foxtail | 5 | 5 | 80 | 60 | 50 | 60 | 100 | 100 | 25 | 50 | 30 | 60 |

TABLE 1-continued

PREEMERGENCE HERBICIDAL ACTIVITY (% CONTROL AT 0.3 kg/ha))

| | | | | | | | | | | | | |
|---|---|---|---|---|---|---|---|---|---|---|---|---|
| Johnsongrass | 10 | 0 | 20 | 0 | 0 | 30 | 30 | 20 | 15 | 40 | 10 | 30 |

| Cmpd. No. | 37 | 40 | 41 | 42 | 43 | 44 | 47 | 48 | 49 | 50 | 51 | 52 |
|---|---|---|---|---|---|---|---|---|---|---|---|---|
| Species | | | | | | | | | | | | |
| Soybean | 10 | 5 | 10 | 10 | 10 | ND | 0 | 5 | 0 | 40 | 40 | 40 |
| Wheat | 20 | 0 | 5 | 20 | 20 | 10 | 0 | 0 | 10 | 10 | 20 | 10 |
| Corn | 10 | 0 | 5 | 10 | 0 | 5 | 5 | 5 | 10 | 10 | 20 | 10 |
| Velvetleaf | 100 | 100 | 60 | 100 | 100 | 100 | 80 | 70 | 100 | 100 | 100 | 100 |
| Morningglory | 100 | 70 | 40 | 90 | 100 | 100 | 70 | 90 | 60 | 80 | 50 | 95 |
| Chickweed | 90 | 100 | 90 | 100 | 100 | 95 | 90 | 100 | 100 | 100 | 100 | 100 |
| Cocklebur | 60 | 0 | 20 | 25 | 30 | 15 | 10 | 20 | 10 | 30 | 30 | 50 |
| Blackgrass | 30 | 70 | ND | ND | 30 | 20 | 30 | 15 | 30 | 20 | 50 | 20 |
| Green foxtail | 70 | 0 | 40 | 90 | 60 | 50 | 20 | 40 | 30 | 50 | 40 | 40 |
| Johnsongrass | 40 | 30 | 30 | 55 | 20 | 20 | 0 | 20 | 10 | 40 | 10 | 30 |

| Cmpd. No. | 53 | 54 | 55 | 56 | 68 | 69 | 76 | 88 | 89 | 90 | 91 | 92 |
|---|---|---|---|---|---|---|---|---|---|---|---|---|
| Species | | | | | | | | | | | | |
| Soybean | 60 | 60 | 50 | 25 | 20 | 0 | 10 | 40 | 30 | 60 | 40 | 35 |
| Wheat | 10 | 0 | 20 | 10 | 30 | 0 | 0 | 20 | 0 | 20 | 20 | 10 |
| Corn | 10 | 0 | 10 | 10 | 0 | 0 | 0 | 10 | 30 | 20 | 0 | 15 |
| Velvetleaf | 100 | 95 | 100 | 100 | 100 | 70 | 100 | 100 | 100 | 100 | 90 | 100 |
| Morningglory | 80 | 95 | 100 | 70 | 100 | 40 | 100 | 100 | 100 | 100 | 70 | 90 |
| Chickweed | 100 | 100 | 100 | 100 | 100 | 100 | 100 | 100 | 100 | 100 | 100 | 90 |
| Cocklebur | 20 | 30 | 30 | 20 | 80 | 40 | 70 | 20 | 80 | 60 | 30 | 50 |
| Blackgrass | 10 | 10 | 0 | 20 | ND | ND | ND | 20 | ND | 30 | 20 | ND |
| Green foxtail | 40 | 80 | 70 | 50 | 40 | 10 | 40 | 60 | 100 | 80 | 75 | 60 |
| Johnsongrass | 40 | 40 | 40 | 20 | 50 | 30 | 0 | 20 | 0 | 30 | 25 | 55 |

| Cmpd. No. | 93 | 97 | 99 | 103 | 128 | 131 | 153 | 157 | 158 | 159 | 181 | 182 |
|---|---|---|---|---|---|---|---|---|---|---|---|---|
| Species | | | | | | | | | | | | |
| Soybean | 20 | 10 | 15 | 10 | 40 | 0 | 0 | 0 | 0 | 0 | 0 | 10 |
| Wheat | 10 | 15 | 10 | 0 | 20 | 0 | 0 | 0 | 10 | 0 | 10 | 20 |
| Corn | 35 | 10 | 10 | 0 | 10 | 0 | 0 | 0 | 10 | 0 | 10 | 10 |
| Velvetleaf | 100 | 100 | 100 | 100 | 70 | 30 | 10 | 0 | 0 | 10 | 100 | 100 |
| Morningglory | 100 | 90 | 100 | 100 | 50 | 40 | 0 | 0 | 0 | 0 | 40 | 90 |
| Chickweed | ND | 100 | 100 | 100 | 60 | 30 | 0 | 40 | 20 | 20 | 95 | 100 |
| Cocklebur | 60 | 60 | 60 | 30 | 10 | 10 | 40 | 20 | 0 | 10 | 20 | 30 |
| Blackgrass | 60 | ND | ND | ND | 20 | 10 | ND | ND | ND | ND | ND | ND |
| Green foxtail | 60 | 75 | 40 | 40 | 30 | 15 | 0 | 0 | 0 | 0 | 40 | 50 |
| Johnsongrass | 40 | 40 | 10 | 0 | 20 | 0 | 20 | 30 | 20 | 30 | 25 | 20 |

| Cmpd. No. | 184 | 185 | 186 | 187 | 188 | 189 | 190 | 191 | 192 | 193 | 194 |
|---|---|---|---|---|---|---|---|---|---|---|---|
| Species | | | | | | | | | | | |
| Soybean | 0 | 15 | 15 | 0 | 0 | 0 | 0 | 30 | 60 | 40 | 10 |
| Wheat | 0 | 0 | 0 | 0 | 20 | 10 | 10 | 30 | 30 | 20 | 0 |
| Corn | 0 | 15 | 10 | 10 | 0 | 10 | 5 | 30 | 10 | 10 | 30 |
| Velvetleaf | 30 | 95 | 90 | 95 | 90 | 95 | 15 | 100 | 100 | 100 | 100 |
| Morningglory | 40 | 100 | 100 | 60 | 80 | 95 | 15 | 95 | 90 | 100 | 70 |
| Chickweed | 80 | 100 | 100 | 100 | 100 | 60 | 0 | 100 | 100 | 100 | 80 |
| Cocklebur | 10 | 10 | 40 | 20 | 35 | 30 | 0 | 80 | 60 | 89 | 15 |
| Blackgrass | 20 | 20 | 40 | ND | ND | 30 | 0 | ND | 70 | 60 | 40 |
| Green foxtail | 30 | 20 | 30 | 60 | 40 | 50 | 20 | 40 | 90 | 80 | 10 |
| Johnsongrass | 0 | 10 | 10 | 50 | 30 | 15 | 5 | 20 | 60 | 40 | 0 |

TABLE 2

POSTEMERGENCE HERBICIDAL ACTIVITY (% CONTROL AT 0.3 kg/ha)

| Cmpd. No. | 1 | 2 | 6 | 7 | 8 | 9 | 19 | 20 | 31 | 32 | 35 | 36 |
|---|---|---|---|---|---|---|---|---|---|---|---|---|
| Species | | | | | | | | | | | | |
| Soybean | 40 | 15 | 50 | 20 | 60 | 40 | 20 | 60 | 70 | 70 | 60 | 85 |
| Wheat | 10 | 5 | 10 | 20 | 10 | 20 | 10 | 30 | 30 | 30 | 20 | 50 |
| Corn | 50 | 30 | 60 | 40 | 65 | 50 | 50 | 80 | 65 | 65 | 60 | 70 |
| Velvetleaf | 60 | 20 | 80 | 80 | 50 | 100 | 100 | 100 | 100 | 100 | 60 | 100 |

TABLE 2-continued

POSTEMERGENCE HERBICIDAL ACTIVITY (% CONTROL AT 0.3 kg/ha)

| | | | | | | | | | | | | |
|---|---|---|---|---|---|---|---|---|---|---|---|---|
| Morningglory | 100 | 90 | 100 | 100 | 80 | 100 | 100 | 100 | 100 | 100 | 100 | 100 |
| Chickweed | 30 | 10 | 40 | 20 | 40 | 80 | ND | 100 | 100 | 100 | 100 | 100 |
| Cocklebur | 50 | 20 | 80 | 15 | 30 | 60 | 100 | 100 | 100 | 100 | 95 | 100 |
| Blackgrass | ND | 5 | ND | 5 | 10 | ND | 80 | 60 | 40 | ND | 20 | ND |
| Green foxtail | 30 | 50 | 60 | 90 | 50 | 70 | 100 | 100 | 50 | 60 | 40 | 90 |
| Johnsongrass | 40 | 5 | 50 | 40 | 30 | 55 | 60 | 30 | 30 | 30 | 20 | 70 |

| Cmpd.No. | 37 | 40 | 41 | 42 | 43 | 44 | 47 | 48 | 49 | 50 | 51 | 52 |
|---|---|---|---|---|---|---|---|---|---|---|---|---|
| Species | | | | | | | | | | | | |
| Soybean | 75 | 70 | 50 | 50 | 70 | 85 | 70 | 60 | 70 | 55 | 60 | 75 |
| Wheat | 30 | 30 | 30 | 20 | 40 | 30 | 20 | 20 | 30 | 30 | 30 | 40 |
| Corn | 65 | 60 | 60 | 55 | 70 | 60 | 90 | 70 | 80 | 50 | 50 | 80 |
| Velvetleaf | 100 | 80 | 60 | 70 | 100 | 100 | 60 | 100 | 60 | 100 | 70 | 80 |
| Morningglory | 100 | 100 | 60 | 60 | 100 | 100 | 100 | 100 | 100 | 90 | 100 | 100 |
| Chickweed | 100 | 80 | 80 | 80 | 100 | 100 | 70 | 100 | 100 | 100 | 70 | 80 |
| Cocklebur | 100 | 65 | 50 | 50 | 100 | 100 | 60 | 80 | 70 | 100 | 60 | 90 |
| Blackgrass | 40 | 30 | 40 | 60 | 30 | 40 | 30 | 25 | 30 | 20 | 30 | 36 |
| Green foxtail | 75 | 50 | 40 | 40 | 60 | 75 | 50 | 40 | 50 | 60 | 50 | 60 |
| Johnsongrass | 50 | 30 | 50 | 40 | 40 | 50 | 50 | 20 | 40 | 40 | 40 | 50 |

| Cmpd. No. | 53 | 54 | 55 | 56 | 68 | 69 | 76 | 88 | 89 | 90 | 91 | 92 |
|---|---|---|---|---|---|---|---|---|---|---|---|---|
| Species | | | | | | | | | | | | |
| Soybean | 80 | 70 | 70 | 75 | 75 | 70 | 95 | 80 | 95 | 80 | 75 | 70 |
| Wheat | 30 | 20 | 30 | 20 | 30 | 10 | 40 | 40 | 30 | 40 | 20 | 30 |
| Corn | 60 | 80 | 60 | 55 | 65 | 60 | 100 | 100 | 55 | 100 | 90 | 60 |
| Velvetleaf | 100 | 75 | 90 | 100 | 100 | 100 | 100 | 100 | 100 | 100 | 100 | 100 |
| Morningglory | 100 | 95 | 100 | 100 | 100 | 95 | 100 | 100 | 100 | 100 | 100 | 100 |
| Chickweed | 80 | 70 | 100 | 100 | 100 | 80 | ND | 100 | ND | 100 | 100 | 100 |
| Cocklebur | 70 | 50 | 70 | 85 | 100 | 100 | 100 | 100 | 100 | 90 | 90 | 100 |
| Blackgrass | 30 | 40 | 20 | 30 | 40 | 20 | 20 | 30 | 30 | 30 | 40 | 50 |
| Green foxtail | 60 | 60 | 70 | 60 | 70 | 50 | 100 | 70 | 100 | 75 | 60 | 60 |
| Johnsongrass | 40 | 40 | 40 | 30 | 45 | 30 | 5 | 60 | 40 | 50 | 40 | 40 |

| Cmpd.No. | 93 | 97 | 99 | 103 | 128 | 131 | 153 | 157 | 158 | 159 | 181 | 182 |
|---|---|---|---|---|---|---|---|---|---|---|---|---|
| Species | | | | | | | | | | | | |
| Soybean | 50 | 65 | 70 | 100 | 60 | 70 | 0 | 10 | 15 | 0 | 60 | 60 |
| Wheat | 40 | 40 | 40 | ND | 20 | 20 | 0 | 0 | 0 | 0 | 30 | 40 |
| Corn | 50 | 80 | 70 | 55 | 60 | 60 | 5 | 30 | 30 | 20 | 60 | 60 |
| Velvetleaf | 100 | 95 | 100 | 100 | 80 | 90 | 0 | 20 | 10 | 10 | 70 | 100 |
| Morningglory | 90 | 100 | 100 | 100 | 95 | 100 | 0 | 5 | 20 | 5 | 95 | 100 |
| Chickweed | 100 | 100 | 100 | ND | 75 | 90 | ND | ND | ND | ND | 90 | 100 |
| Cocklebur | 100 | 100 | 100 | 100 | 70 | 100 | 0 | 5 | 0 | 0 | 70 | 90 |
| Blackgrass | 20 | 60 | 60 | 20 | 20 | 30 | ND | ND | ND | ND | 30 | 70 |
| Green foxtail | 40 | 60 | 100 | 100 | 80 | 50 | 50 | 10 | 20 | 50 | 50 | 70 |
| Johnsongrass | 30 | 50 | 70 | ND | 60 | 30 | 0 | 5 | 25 | 20 | 40 | 60 |

| Cmpd. No. | 184 | 185 | 186 | 187 | 188 | 189 | 190 | 191 | 192 | 193 | 194 |
|---|---|---|---|---|---|---|---|---|---|---|---|
| Species | | | | | | | | | | | |
| Soybean | 60 | 70 | 70 | 65 | 60 | 70 | 50 | 60 | 60 | 60 | 70 |
| Wheat | 10 | 30 | 30 | 20 | 40 | 30 | 10 | 40 | 40 | 50 | 30 |
| Corn | 60 | 60 | 60 | 70 | 60 | 60 | 60 | 5 | 40 | 60 | 55 |
| Velvetleaf | 70 | 100 | 100 | 90 | 80 | 70 | 60 | 100 | 100 | 100 | 80 |
| Morningglory | 90 | 100 | 100 | 100 | 90 | 100 | 100 | 100 | 100 | 100 | 100 |
| Chickweed | 90 | 100 | 100 | 100 | 100 | 80 | 50 | 100 | 100 | 100 | 100 |
| Cocklebur | 70 | 90 | 100 | 70 | 60 | 70 | 40 | 100 | 100 | 80 | 100 |
| Blackgrass | 30 | 40 | 40 | ND | 50 | 40 | 15 | 60 | 30 | 50 | 30 |
| Green foxtail | 40 | 60 | 50 | 50 | 40 | 50 | 50 | 60 | 90 | 100 | 50 |
| Johnsongrass | 30 | 40 | 40 | 40 | 50 | 40 | 20 | 50 | 40 | 40 | 30 |

Herbicidal compositions are prepared by combining herbicidally effective amounts of the active compounds with adjuvants and carriers normally employed in the art for facilitating the dispersion of active ingredients for the particular utility desired, recognizing the fact that the formulation and mode of application of a toxicant may affect the activity of the material in a given application. Thus, for agricultural use the present herbicidal compounds may be formulated as granules of relatively large particle size, as water-soluble or water-dispersible granules, as powdery dusts, as wettable powders, as emulsifiable concentrates, as solutions, or as any of several other known types of formulations, depending on the desired mode of application. It is to be understood that the amounts specified in this specification are intended to be approximate only, as if the word "about" were placed in front of the amounts specified.

These herbicidal compositions may be applied either as water-diluted sprays, or dusts, or granules to the areas in which suppression of vegetation is desired. These formulations may contain as little as 0.1%, 0.2% or 0.5% to as much as 95% or more by weight of active ingredient.

Dusts are free flowing admixtures of the active ingredient with finely divided solids such as talc, natural clays, kieselguhr, flours such as walnut shell and cottonseed flours, and other organic and inorganic solids which act as dispersants and carriers for the toxicant; these finely divided solids have an average particle size of less than about 50 microns. A typical dust formulation useful herein is one containing 1.0 part or less of the herbicidal compound and 99.0 parts of talc.

Wettable powders, also useful formulations for both pre- and post-emergence herbicides, are in the form of finely divided particles which disperse readily in water or other dispersant. The wettable powder is ultimately applied to the soil either as a dry dust or as an emulsion in water or other liquid. Typical carriers for wettable powders include Fuller's earth, kaolin clays, silicas, and other highly absorbent, readily wet inorganic diluents. Wettable powders normally are prepared to contain about 5–80% of active ingredient, depending on the absorbency of the carrier, and usually also contain a small amount of a wetting, dispersing or emulsifying agent to facilitate dispersion. For example, a useful wettable powder formulation contains 80.0 parts of the herbicidal compound, 17.9 parts of Palmetto clay, and 1.0 part of sodium lignosulfonate and 0.3 part of sulfonated aliphatic polyester as wetting agents. Additional wetting agent and/or oil will frequently be added to the tank mix for post-emergence application to facilitate dispersion on the foliage and absorption by the plant.

Other useful formulations for herbicidal applications are emulsifiable concentrates (ECs) which are homogeneous liquid compositions dispersible in water or other dispersant, and may consist entirely of the herbicidal compound and a liquid or solid emulsifying agent, or may also contain a liquid carrier, such as xylene, heavy aromatic naphthas, isphorone, or other non-volatile organic solvents. For herbicidal application these concentrates are dispersed in water or other liquid carrier and normally applied as a spray to the area to be treated. The percentage by weight of the essential active ingredient may vary according to the manner in which the composition is to be applied, but in general comprises 0.5 to 95% of active ingredient by weight of the herbicidal composition.

Flowable formulations are similar to ECs except that the active ingredient is suspended in a liquid carrier, generally water. Flowables, like ECs, may include a small amount of a surfactant, and will typically contain active ingredients in the range of 0.5 to 95%, frequently from 10 to 50%, by weight of the composition. For application, flowables may be diluted in water or other liquid vehicle, and are normally applied as a spray to the area to be treated.

Typical wetting, dispersing or emulsifying agents used in agricultural formulations include, but are not limited to, the alkyl and alkylaryl sulfonates and sulfates and their sodium salts; alkylaryl polyether alcohols; sulfated higher alcohols; polyethylene oxides; sulfonated animal and vegetable oils; sulfonated petroleum oils; fatty acid esters of polyhydric alcohols and the ethylene oxide addition products of such esters; and the addition product of long-chain mercaptans and ethylene oxide. Many other types of useful surface-active agents are available in commerce. Surface-active agents, when used, normally comprise 1 to 15% by weight of the composition.

Other useful formulations include suspensions of the active ingredient in a relatively non-volatile solvent such as water, corn oil, kerosene, propylene glycol, or other suitable solvents.

Still other useful formulations for herbicidal applications include simple solutions of the active ingredient in a solvent in which it is completely soluble at the desired concentration, such as acetone, alkylated naphthalenes, xylene, or other organic solvents. Granular formulations, wherein the toxicant is carried on relative coarse particles, are of particular utility for aerial distribution or for penetration of cover crop canopy. Pressurized sprays, typically aerosols wherein the active ingredient is dispersed in finely divided form as a result of vaporization of a low boiling dispersant solvent carrier, such as the Freon fluorinated hydrocarbons, may also be used. Water-soluble or water-dispersible granules are free-flowing, non-dusty, and readily water-soluble or water-miscible. The soluble or dispersible granular formulations described in U.S. Pat. No. 3,920,442 are useful herein with the present herbicidal compounds. In use by the farmer on the field, the granular formulations, emulsifiable concentrates, flowable concentrates, solutions, etc., may be diluted with water to give a concentration of active ingredient in the range of say 0.1% or 0.2% to 1.5% or 2%.

The active herbicidal compounds of this invention may be formulated and/or applied with insecticides, fungicides, nematicides, plant growth regulators, fertilizers, or other agricultural chemicals and may be used as effective soil sterilants as well as selective herbicides in agriculture. In applying an active compound of this invention, whether formulated alone or with other agricultural chemicals, an effective amount and concentration of the active compound is of course employed; the amount may be as low as, e.g. about 1 to 250 g/ha, preferably about 4 to 30 g/ha. For field use, where there are losses of herbicide, higher application rates (e.g., four times the rates mentioned above) may be employed.

The active herbicidal compounds of the present invention may also be used in combination with other herbicides. Such herbicides include, for example: N-(phosphonomethyl) glycine ("glyphosate"); aryloxyalkanoic acids such as (2,4-dichlorophenoxy)acetic acid ("2,4-D"), (4-chloro-2-methylphenoxy)acetic acid ("MCPA"), (+/−)-2-(4-chloro-2-methylphenoxy)propanoic acid (MCPP); ureas such as N,N-dimethyl-N'-[4-(1-methylethyl)phenyl]urea ("isoproturon"); imidazolinones such as 2-[4,5-dihydro-4-methyl-4-(1-methylethyl)-5-oxo-1H-imidazol-2-yl]-3-pyridinecarboxylic acid ("imazapyr"), a reaction product comprising (+/−)-2-[4,5-dihydro-4-methyl-4-(1-methylethyl)-5-oxo-1H-imidazol-2-yl]-4-methylbenzoic acid and (+/−)-2-[4,5-dihydro-4-methyl-4-(1-methylethyl)-5-oxo-1H-imidazol-2-yl]-5-methylbenzoic acid ("imazamethabenz"), (+/−)-2-[4,5-dihydro-4-methyl-4-(1-methylethyl)-5-oxo-1H-imidazol-2-yl]-5-ethyl-3-pyridinecarboxylic acid ("imazethapyr") and (+/−)-2-[4,5-dihydro-4-methyl-4-(1-methylethyl)-5-oxo-1H-imidazol-2-yl]-3-quinolinecarboxylic acid ("imazaquin"); diphenyl ethers such as 5-[2-chloro-4-(trifluoromethyl)phenoxy]-2-nitrobenzoic acid ("acifluorfen"), methyl 5-(2,4-dichlorophenoxy)-2-nitrobenzoate ("bifenox"), and 5-[2-chloro-4-(trifluoromethyl)phenoxy]-N-(methylsulfonyl)-2-nitrobenzamide ("fomasafen"); hydroxybenzonitriles such as 4-hydroxy-3,5-diiodobenzonitrile ("ioxynil") and 3,5-dibromo-4-hydroxybenzonitrile ("bromoxynil"); sulfonylureas such as 2-[[[[(4-chloro-6-methoxy-2-pyrimidinyl)

amino]carbonyl]amino]sulfonyl]benzoic acid ("chlorimuron"), 2-chloro-N-[[(4-methoxy-6-methyl-1,3,5-triazin-2-yl)amino]-carbonyl]benzenesulfonamide ("chlorsulfuron"), 2-[[[[[(4,6-dimethoxy-2-pyrimidinyl) amino]carbonyl]amino]sulfonyl]methyl]benzoic acid ("bensulfuron"), 2-[[[[(4,6-dimethoxy-2-pyrimidinyl) amino]carbonyl]amino]sulfonyl]-1-methyl-1H-pyrazol-4-carboxylic acid ("pyrazosulfuron"), 3-[[[[(4-methoxy-6-methyl-1,3,5-triazin-2-yl)amino]carbonyl]amino]sulfonyl]-2-thiophenecarboxylic acid ("thifensulfuron"), and 2-(2-chloroethoxy)-N-[[(4-methoxy-6-methyl-1,3,5-triazin-2-yl) amino]carbonyl]benzenesulfonamide ("triasulfuron"); 2-(4-aryloxyphenoxy)-alkanoic acids such as (+/−)-2-[4-[(6-chloro-2-benzoxazolyl)oxy]phenoxy]propanoic acid ("fenoxaprop"), (+/−)-2-[4-[[5-(trifluoromethyl)-2-pyridinyl]oxy]phenoxy]-propanoic acid ("fluazifop"), (+/−)-2-[4-(6-chloro-2-quinoxalinyl)oxy]phenoxy]-propanoic acid ("quizalofop"), and (+/−)-2-[-(2,4-dichlorophenoxy) phenoxy]-propanoic acid ("diclofop"); benzothiadiazinones such as 3-(1-methylethyl)-1H-2,1,3-benzothiadiazin-4(3 H)-one 2,2-dioxide ("bentazone"); 2-chloroacetanilides such as N-butoxymethyl)-2-chloro-2', 6'-diethylacetanilide ("butachlor"); arenecarboxylic acids such as 3,6-dichloro-2-methoxybenzoic acid ("dicamba"); and pyridyloxyacetic acids such as [(4-amino-3,5-dichloro-6-fluoro-2-pyridinyl) oxy]acetic acid ("fluroxypyr").

It is apparent that various modifications may be made in the formulations and application of the compounds of the present invention without departing from the inventive concepts herein, as defined in the claims.

What is claimed is:

1. An herbicidal compound having the chemical structure:

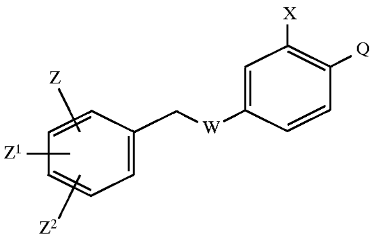

wherein:

Q is

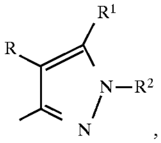

, or

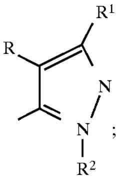

;

R is halogen;

$R^1$ is lower alkyl, lower alkoxy, lower haloalkyl, lower haloalkoxy, lower alkylthio, lower alkylsulfonlyl, or lower alkylsulfinyl;

$R^2$ is lower alkyl, or lower haloalkyl;

X is H, halogen, or lower alkyl;

W is O or S;

Z, $Z^1$, and $Z^2$ are independently selected from H, halogen, straight or branched chain lower alkyl, lower haloalkyl, lower alkoxy, lower haloalkoxy, cyano, lower cyanoalkoxy, nitro, phenyl, or phenoxy; or Z and $Z^1$ are adjacent to each other on the phenyl ring and, taken together, are $-(CH_2)_4-$; or $Z^2$ is OA in the 2-, 3- or 4-position of the phenyl ring;

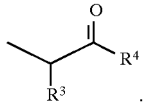

;

A is $R^3$ is H, lower alkyl, or halo;

$R^4$ is OH, straight or branched chain lower alkoxy, lower haloalkoxy, (lower alkoxy)-(lower alkoxy), (lower alkoxy)-(lower alkoxy)-(lower alkoxy), (lower alkoxy) -carbonyl-(lower alkoxy), amino, lower alkylamino, lower dialkylamino, lower alkoxyamino, lower alkylsulfonylamino, lower haloalkylsulfonylamino, lower (alkyl)(alkylsulfonyl)amino, or an agriculturally acceptable salt thereof; and $R^5$ is halogen or lower alkyl ester.

2. A compound of claim 1 wherein $Z^2$ is OA.

3. A compound of claim 2 wherein Q is

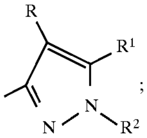

; and $R^3$ is H or lower alkyl.

4. A compound of claim 3 wherein R is a halogen, $R^1$ is lower haloalkoxy, and $R^3$ is lower alkyl.

5. A compound of claim 4 wherein R is chloro, $R^1$ is difluoromethoxy, and R is methyl.

6. A process of controlling undesired plant growth, comprising application to the locus where the undesired plants are growing or are expected to grow, an herbicidally effective amount of a compound of claim 1.

7. An herbicidal composition comprising an herbicidally effective amount of a compound of claim 1, and an herbicidally compatible carrier therefor.

* * * * *